(12) United States Patent
Takahashi et al.

(10) Patent No.: US 12,409,565 B2
(45) Date of Patent: Sep. 9, 2025

(54) ROBOTIC SURGICAL SYSTEM, SURGICAL ROBOT, AND ROBOTIC SURGICAL METHOD

(71) Applicant: KAWASAKI JUKOGYO KABUSHIKI KAISHA, Kobe (JP)

(72) Inventors: Kaoru Takahashi, Kobe (JP); Hidenori Tani, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 533 days.

(21) Appl. No.: 17/895,105

(22) Filed: Aug. 25, 2022

(65) Prior Publication Data

US 2023/0061446 A1 Mar. 2, 2023

(30) Foreign Application Priority Data

Aug. 26, 2021 (JP) ................. 2021-138284
Aug. 10, 2022 (JP) ................. 2022-128113

(51) Int. Cl.
*B25J 15/02* (2006.01)
*A61B 34/00* (2016.01)
(Continued)

(52) U.S. Cl.
CPC .......... *B25J 15/0206* (2013.01); *A61B 34/37* (2016.02); *A61B 34/70* (2016.02);
(Continued)

(58) Field of Classification Search
CPC ......... A61B 17/29; A61B 34/37; A61B 34/70; A61B 90/37; A61B 2017/00212;
(Continued)

(56) References Cited

U.S. PATENT DOCUMENTS 4,696,501 A * 9/1987 Webb ..................... B25J 13/082
414/730
4,783,107 A * 11/1988 Parker ................. B25J 15/0004
294/213

(Continued)

FOREIGN PATENT DOCUMENTS

JP 2020-536685 A 12/2020
WO 2019/221754 A1 11/2019

*Primary Examiner* — Wade Miles
*Assistant Examiner* — James Brian Chin
(74) *Attorney, Agent, or Firm* — METROLEX IP LAW GROUP, PLLC; Robert L. Scott, Esq.

(57) ABSTRACT

A robotic surgical system according to an embodiment may include: a surgical instrument including a pair of jaw members; an operation handle; and a surgical robot that includes a robot arm to which the surgical instrument is attached and which includes a drive part to drive a driven member, and a controller configured to drive the drive part based on a command jaw opening angle associated with an input to the input device for controlling an opening angle between the pair of jaw members. The controller is configured, when it is determined that a current value of the drive part excesses a predetermined threshold value during a closing operation of the pair of jaw members, to drive the drive part in a restriction mode in which a magnitude of the command jaw opening angle is restricted.

20 Claims, 12 Drawing Sheets

(51) Int. Cl.
    *A61B 34/37*         (2016.01)
    *A61B 17/00*         (2006.01)
    *A61B 17/29*         (2006.01)
    *A61B 34/30*         (2016.01)
    *A61B 90/00*         (2016.01)

(52) U.S. Cl.
    CPC ............... *A61B 2017/00212* (2013.01); *A61B 2017/2939* (2013.01); *A61B 2017/2946* (2013.01); *A61B 2034/301* (2016.02); *A61B 2090/067* (2016.02)

(58) Field of Classification Search
    CPC .... A61B 2017/2939; A61B 2017/2946; A61B 2034/301; A61B 2090/067; A61B 34/71; A61B 2017/00973; A61B 2034/2059; A61B 2090/373; B25J 15/0206
    See application file for complete search history.

(56) References Cited

U.S. PATENT DOCUMENTS

| | | | | |
|---|---|---|---|---|
| 5,368,015 | A * | 11/1994 | Wilk | A61B 34/35 128/903 |
| 5,624,398 | A * | 4/1997 | Smith | A61B 34/70 604/95.01 |
| 8,597,182 | B2 * | 12/2013 | Stein | A61B 34/37 600/214 |
| 9,566,124 | B2 * | 2/2017 | Prisco | A61B 34/35 |
| 10,493,634 | B1 * | 12/2019 | Alqasemi | B25J 15/0028 |
| 11,751,966 | B2 * | 9/2023 | Hulford | A61B 34/25 606/130 |
| 12,242,662 | B2 * | 3/2025 | Verner | G06F 3/038 |
| 2002/0082612 | A1 * | 6/2002 | Moll | G16H 40/63 606/130 |
| 2006/0161136 | A1 * | 7/2006 | Anderson | A61B 34/37 606/1 |
| 2007/0151390 | A1 * | 7/2007 | Blumenkranz | G01L 5/22 74/490.06 |
| 2011/0196199 | A1 * | 8/2011 | Donhowe | A61B 5/065 600/102 |
| 2014/0081455 | A1 * | 3/2014 | Goldberg | A61B 90/98 700/250 |
| 2015/0258690 | A1 * | 9/2015 | Naitou | B25J 19/06 901/46 |
| 2019/0328472 | A1 * | 10/2019 | Tojo | A61B 17/3423 |
| 2020/0055152 | A1 * | 2/2020 | Chavan Dafle | G01B 5/241 |
| 2021/0022738 | A1 * | 1/2021 | Weir | A61B 34/37 |
| 2022/0409317 | A1 * | 12/2022 | Ichii | B25J 9/1689 |
| 2023/0061446 | A1 * | 3/2023 | Takahashi | A61B 90/37 |
| 2023/0190397 | A1 * | 6/2023 | Turner | A61B 34/74 606/1 |
| 2024/0189051 | A1 * | 6/2024 | Lynch | A61B 34/30 |
| 2025/0080025 | A1 * | 3/2025 | Okumatsu | H02P 23/14 |

* cited by examiner

ROBOTIC SURGICAL SYSTEM, SURGICAL ROBOT, AND ROBOTIC SURGICAL METHOD

CROSS REFERENCE TO RELATED APPLICATIONS

This application claims priority to Japanese Patent Applications No. 2021-138284 filed on Aug. 26, 2021 and No. 2022-128113 filed on Aug. 10, 2022, the entire contents of all of which are incorporated herein by reference.

BACKGROUND

The disclosure may relate to a robotic surgical system, a surgical robot, and a robotic surgical method.

In a related art, there has been known a robotic surgical system including a surgical instrument including a pair of jaw members.

JP2020-536685 discloses a surgical robot system (a robotic surgical system) that includes a surgical tool including a pair of jaw members and a robot control system configured to control a grasping force and an angle between the pair of jaw members by using a position controller and a grasping force controller. For the grasping force controller to obtain (detect) tensions of cables that drive the pair of jaw members, the surgical robot system includes load cells or torque sensors. The grasping force controller controls, based on the tensions of the cables measured by the load cells or the torque sensors, the grasping force to a desired grasping force.

SUMMARY

However, although the surgical robot system disclosed in JP2020-53665 can generate the desire grasping force, the grasping force controller needs be provided with the load cells or the torque sensors to measure the tensions of the cables of the surgical tool. In such a case, there may be a problem that the structure around the cables (elongate elements) becomes complicated.

An object of an embodiment of the disclosure may be to provide a robotic surgical system, a surgical robot, and a robotic surgical method that can generate an appropriate grasping force while suppressing a structure around elongate elements from being complicated.

An first aspect of the disclosure may be a robotic surgical system that includes: a surgical instrument including a pair of jaw members configured to be driven by elongate elements connected to a driven member so as to be opened and closed to grasp an object; an input device to which a command for opening and closing the pair of jaw members is to be input; and a surgical robot that includes a robot arm to which the surgical instrument is attached and which includes a drive part configured to drive the driven member, and a controller configured to drive the drive part based on a command jaw opening angle associated with an input to the input device for controlling an opening angle between the pair of jaw members. The controller is configured to determine whether or not a current value of the drive part excesses a predetermined threshold value during a closing operation of the pair of jaw members and, when it is determined that the current value of the drive part excesses the predetermined threshold value, to drive the drive part in a restriction mode in which a magnitude of the command jaw opening angle is restricted.

According to the first aspect, the controller is configured to determine whether or not the current value of the drive part exceeds the predetermined threshold value during the closing operation of the pair of jaw members, and when it is determined that the current value of the drive part exceeds the predetermined threshold value, to drive the drive part in the restriction mode in which the magnitude of the command jaw opening angle is restricted. With this configuration, since the drive part is driven in the restriction mode in which the magnitude of the command jaw opening angle is restricted when it is determined that the motor current value of the drive part exceeds the predetermined threshold value during the operation of closing the pair of jaw members, it is possible to prevent the grasping force from becoming excessive. As a result, an appropriate grasping force can be obtained. Further, since the magnitude of the command jaw opening angle is restricted, it is not necessary to provide load cells or torque sensors to the elongate elements. Therefore, it is possible to make a structure around the elongate elements less complicated than a case where the load cells or the torque sensors are provided to the elongate elements. As a result, it is possible to provide a robotic surgical system that is capable of providing an appropriate grasping force while preventing the structure around the elongate elements from being complicated.

An second aspect of the disclosure may be a robotic surgical method for a robotic surgical system, wherein the robotic surgical system includes: a surgical instrument including a pair of jaw members configured to be driven by elongate elements connected to a driven member so as to be opened and closed to grasp an object; an input device to which a command for opening and closing the pair of jaw members is to be input; and a surgical robot including a robot arm to which the surgical instrument is attached and which includes a drive part configured to drive the driven member. The robotic surgical method may include: obtaining a command jaw opening angle that is associated with an input to the input device for controlling an opening angle between the pair of jaw members; and driving the drive part based on the command jaw opening angle. The driving of the drive part includes: determining whether or not a current value of the drive part excesses a predetermined threshold value during a closing operation of the pair of jaw members; and when it is determined that the current value of the drive part excesses the predetermined threshold value, driving the drive part in a restriction mode in which a magnitude of the command jaw opening angle is restricted.

According to the second aspect, the driving of the drive part includes: determining whether or not the current value of the drive part exceeds the predetermined threshold value during the closing operation of the pair of jaw members; and when it is determined that the current value of the drive part exceeds the predetermined threshold value, driving the drive part in a restriction mode in which the magnitude of the command jaw opening angle is restricted. With this configuration, since the drive part is driven in the restriction mode in which the magnitude of the command jaw opening angle is restricted when it is determined that the motor current value of the drive part exceeds the predetermined threshold value during the operation of closing the pair of jaw members, it is possible to prevent the grasping force from becoming excessive. As a result, an appropriate grasping force can be obtained. Further, since the magnitude of the command jaw opening angle is restricted, it is not necessary to provide load cells or torque sensors to the elongate elements. Therefore, it is possible to make a structure around the elongate elements less complicated than a case where the load cells or the torque sensors are provided to the elongate elements. As a result, it is possible to provide a robotic surgical method that is capable of providing an appropriate grasping force while preventing the structure around the elongate elements from being complicated.

An third aspect of the disclosure may be a surgical robot that may include: a surgical instrument including a pair of jaw members configured to be driven by elongate elements connected to a driven member so as to be opened and closed to grasp an object; a robot arm to which the surgical instrument is attached and including a drive part configured to drive the driven member; a controller configured to drive the drive part based on a command jaw opening angle for an opening angle between the pair of jaw members. The controller is configured to determine whether or not a current value of the drive part exceeds a predetermined threshold value during a closing operation of the pair of jaw members, and when it is determined that the current value of the drive part exceeds the predetermined threshold value, to drive the drive part in a restriction mode in which a magnitude of the command jaw opening angle is restricted.

According to the third aspect, the controller is configured to determine whether or not the current value of the drive part exceeds the predetermined threshold value during the closing operation of the pair of jaw members, and when it is determined that the current value of the drive part exceeds the predetermined threshold value, to drive the drive part in the restriction mode in which the magnitude of the command jaw opening angle is restricted. With this configuration, when it is determined that the motor current value of the drive part exceeds the predetermined threshold value during the closing operation of the pair of jaw members, the drive part is driven in the restriction mode in which the magnitude of the command jaw opening angle is restricted. Therefore, it is possible to prevent the grasping force from becoming excessive. As a result, an appropriate grasping force can be obtained. Further, since the magnitude of the command jaw opening angle is restricted, it is not necessary to provide load cells or torque sensors to the elongate elements. Therefore, it is possible to make a structure around the elongate elements less complicated than a case where the load cells or the torque sensors are provided to the elongate elements. As a result, it is possible to provide a surgical robot that is capable of providing an appropriate grasping force while preventing the structure around the elongate elements from being complicated.

DETAILED DESCRIPTION

Figure 1:
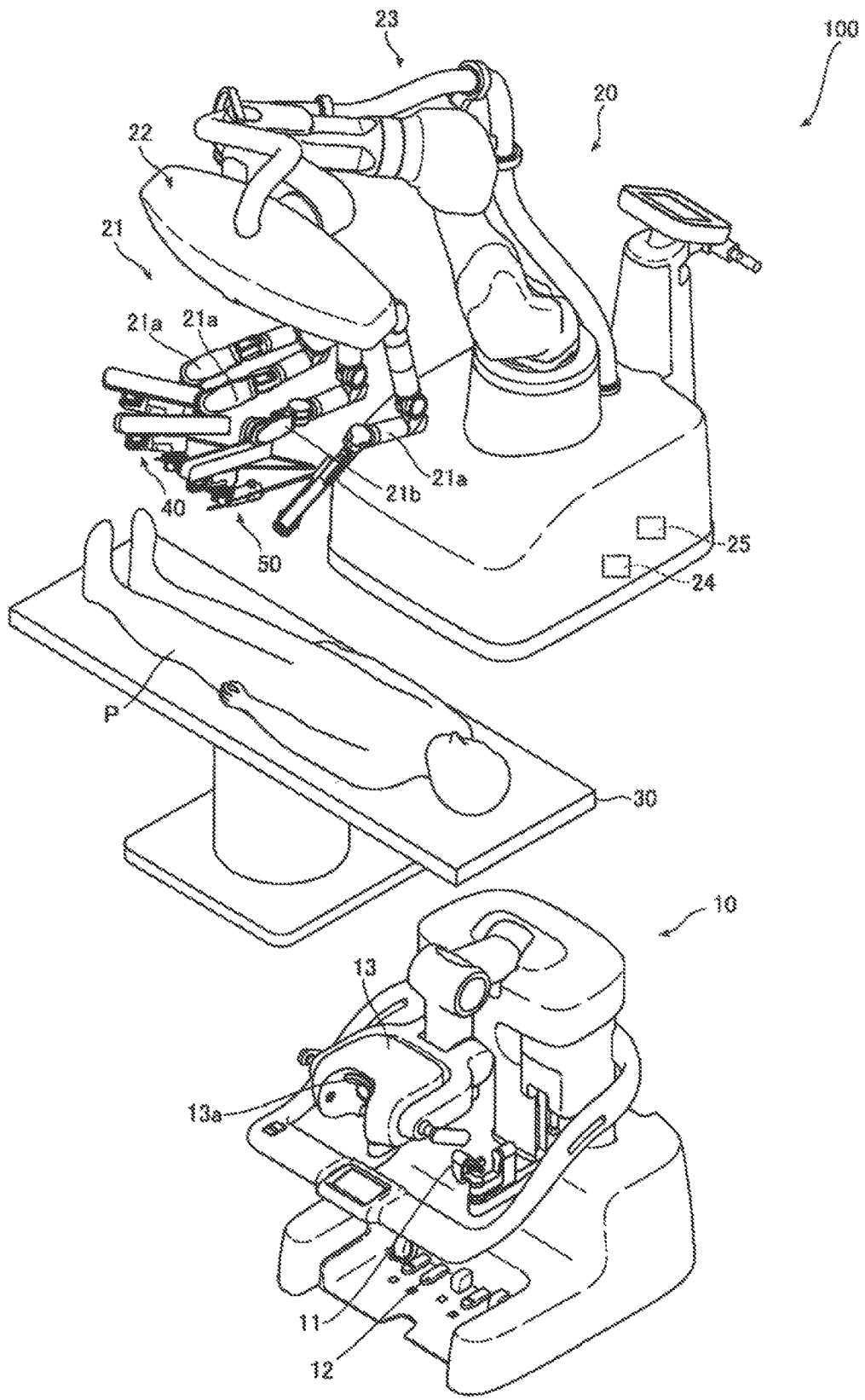
FIG. 1 is a diagram illustrating a configuration of a robotic surgical system according to a first embodiment.

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

First Embodiment (Configuration of Robotic Surgical System)

A configuration of a robotic surgical system 100 according to a first embodiment is described with reference to FIGS. 1 and 2.

As illustrated in FIG. 1, the robotic surgical system 100 includes a remote control apparatus 10 and a patient-side apparatus 20.

The remote control apparatus 10 is provided to remotely control medical equipment provided for the patient-side apparatus 20. When an operator, as a surgeon, inputs an action mode instruction to be executed by the patient-side apparatus 20, to the remote control apparatus 10, the remote control apparatus 10 transmits the action mode instruction to the patient-side apparatus 20 through a controller 24.

In response to the action mode instruction transmitted from the remote control apparatus 10, the patient-side apparatus 20 operates the medical equipment, including surgical instruments 40 attached to robot arms 21*a* and an endoscope 50 attached to a robot arm 21*b*. This allows minimally invasive surgery. Note that the patient-side apparatus 20 is an example of a surgical robot or a surgery assist robot. The controller 24 is an example of a controller or a control device.

The patient-side apparatus 20 constitutes an interface to perform a surgery for a patient P. The patient-side apparatus 20 is positioned beside an operation table 30 on which the patient P is laid. The patient-side apparatus 20 includes plural robot arms 21*a* and 21*b*. One (21*b*) of the robot arms holds the endoscope 50 and the other robot arms (21*a*) hold the surgical instruments 40. The robot arms 21*a* and 21*b* are commonly supported by an arm base 22. Each of the plural robot arms 21*a* and 21*b* includes plural joints. Each joint includes a driver provided with a servo-motor and a position detector such as an encoder. The robot arms 21*a* and 21*b* are configured so that the medical equipment attached to each of the robot arms 21*a* and 21*b* is controlled by a driving signal given through the controller 24 and performs a desired movement.

The arm base 22 is supported by a positioner 23 placed on the floor of an operation room. The positioner 23 includes a vertical articulated robot. The positioner 23 is configured to move the position of the arm base 22 three-dimensionally. The controller 24 is a control circuit including an arithmetic unit such as a CPU and/or the like, and a memory such as a ROM, a RAM, and/or the like.

The surgical instruments 40 as the medical equipment are detachably attached to the distal ends of the robot arms 21*a*. Each surgical instrument 40 includes: a housing 41 (see FIG. 4) which is to be attached to the robot arm 21*a*; an elongated shaft 42 (see FIG. 4); and an end effector 43 (see FIG. 4) which is provided at a tip portion (a distal end portion) of the shaft 42. The end effector 43 may be grasping forceps, scissors, a hook, a high-frequency knife, a snare wire, a clamp, a stapler, a clip applier, an electric knife, or a needle, for example. The end effector 43 is not limited to those and can be various types of treatment tools. In surgeries using the patient-side apparatus 20, the robot arms 21*a* introduce the surgical instruments 40 into the body of the patient P through a cannula (trocar) placed on the body surface of the patient P. The end effectors 43 of the surgical instruments 40 are then located near a surgery site.

To the distal end of the robot arm 21*b*, the endoscope 50 as the medical equipment is detachably attached. The endoscope 50 captures an image in a body cavity of the patient P. The captured image is outputted to the remote control apparatus 10. The endoscope 50 may be a 3D endoscope capable of capturing a three-dimensional image or a 2D endoscope. In surgeries using the patient-side apparatus 20, the robot arm 21*b* introduces the endoscope 50 into the body of the patient P through a trocar placed on the body surface of the patient P. The endoscope 50 is then located near the surgery site.

The remote control apparatus 10 constitutes an interface with the operator. The remote control apparatus 10 is an apparatus that allows the operator to operate the medical equipment attached to the robot arms 21*a* and 22*b*. Specifically, the remote control apparatus 10 is configured to transmit action mode instructions which are inputted by the operator and are to be executed by the surgical instruments 40 and endoscope 50, to the patient-side apparatus 20 through the controller 24. The remote control apparatus 10 is installed beside the operation table 30 so that the operator can see the condition of the patient P very well while operating the remote control apparatus 10, for example. The remote control apparatus 10 may be configured to transmit action mode instructions wirelessly and installed in a room different from the operation room where the operation table 30 is installed.

The action modes to be executed by the surgical instruments 40 include modes of actions to be taken by each surgical instrument 40 (a series of positions and postures) and actions to be executed by the function of each surgical instrument 40. When the surgical instrument 40 is a pair of grasping forceps, for example, the action modes to be executed by the surgical instrument 40 include roll and pitch positions of the wrist of the end effector 43 and actions to open and close the jaws. When the surgical instrument 40 is a high-frequency knife, the action modes to be executed by the surgical instrument 40 include vibration of the high-frequency knife, specifically, supply of current to the high-frequency knife. When the surgical instrument 40 is a snare wire, the action modes to be executed by the surgical instrument 40 include a capturing action and an action to release the captured object. Further, the action modes may include an action to supply current to a bipolar or monopolar instrument to burn off the surgery site.

The action modes to be executed by the endoscope 50 include the position and posture of the tip of the endoscope 50 and setting of the zoom magnification, for example.

Figure 2:
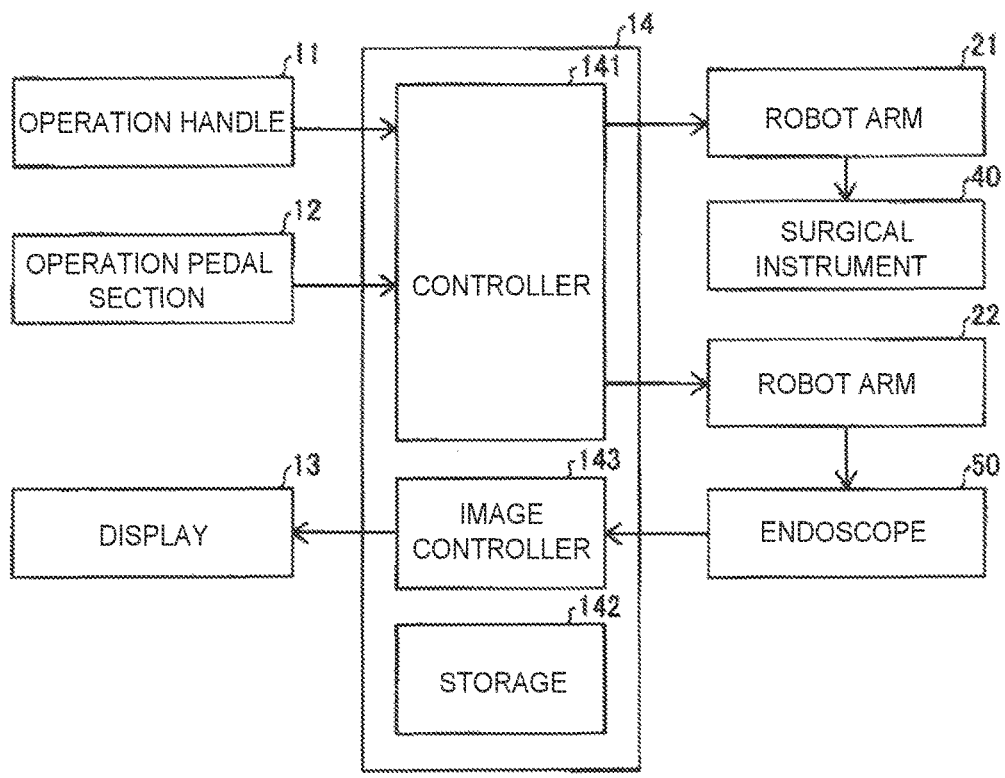
FIG. 2 is a block diagram illustrating a view of a control-related configuration of the robotic surgical system according to a first embodiment.

As illustrated in FIGS. 1 and 2, the remote control apparatus 10 includes operation handles 11, an operation pedal section 12, a display 13, and a control apparatus 14. Note that the operation handle 11 is an example of an input device.

The operation handles 11 are provided in order to remotely operate medical equipment attached to the robot arms 21*a* and 21*b*. Specifically, the operation handles 11 accept operations by the operator for operating the medical equipment (the surgical instruments 40 and endoscope 50). The operation handles 11 are composed of two operation handles 11 arranged side by side in the horizontal direction. One of the two operation handles 11 is operated by the right hand of the operator while the other of the two operation handle 11 is operated by the left hand of the operator.

The operation handles 11 extend from the rear side of the remote control apparatus 10 toward the front side. The operation handles 11 are configured to move in a predetermined three-dimensional operation region. Specifically, the operation handles 11 are configured to be movable in a vertical direction, a horizontal direction, a front-rear direction, and a rotational direction.

Figure 3:
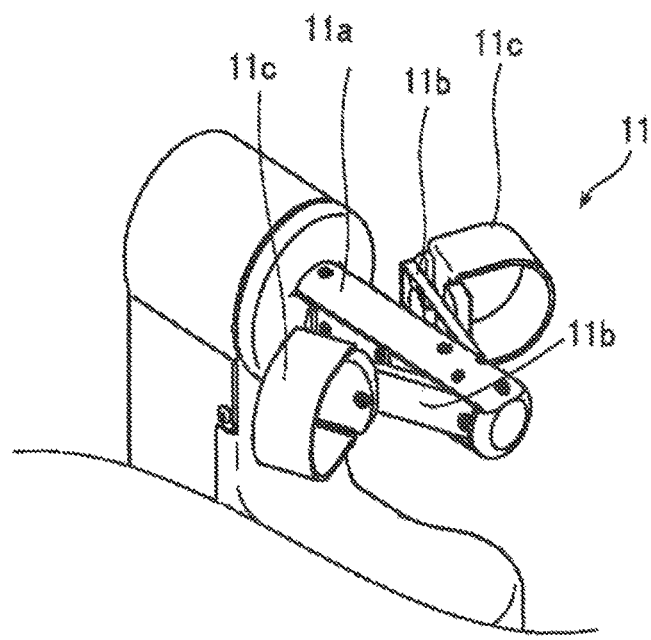
FIG. 3 is a diagram illustrating a view of a configuration of an operation handle according to a first embodiment.

As illustrated in FIG. 3, the operation handles 11 are hand controllers to be operated by the hands of the operator. The operation handle 11 includes a support member 11*a*, a pair of grip members 11*b* provided on both sides of the support member 11*a* with the support member 11*a* being interposed between the pair of grip members 11*b*, and a finger insertion portion 11*c* provided in each of the pair of grip members 11*b*. The operator inserts fingers (such as (thumb, middle finger, etc.) into the pair of finger insertion portions 11*c* to operate the operation handle 11. That is, a proximal end of each of the pair of grip members 11b is rotatably connected to a support member 11a. By increasing or decreasing an opening angle between the pair of grip members 11b (a grip opening angle), the opening angle between a pair of jaw members 43a and 43b, which will be described later, is changed. A command for opening and closing the pair of jaw members 43a and 43b is input to the operation handle 11. The opening angle between the pair of grip members 11b is detected by a sensor, for example. For example, a hole sensor is provided in the support member 11a of the operation handle 11 and a magnet is provided in each of one or both of the pair of grip members 11b of the operation handle 11, so that the opening angle between the pair of grip members 11b can be detected. Or, a hole sensor is provided in one of the pair of grip members 11b of the operation handle 11 and a magnet is provided in the other of the pair of grip members 11b of the operation handle 11, so that the opening angle between the pair of grip members 11b can be detected. The signal regarding the detected opening angle between the pair of grip members 11b is converted by a later-described controller 141 or the controller 24 to a command opening angle (a command jaw opening angle) regarding the opening angle θ between the pair of jaw members 43a and 43b.

As illustrated in FIG. 1, the remote control apparatus 10 and patient-side apparatus 20 constitute a master-slave system in terms of controlling movements of the robot arms 21a and the robot arm 21b. The operation handles 11 constitute an operating part on the master side in the master-slave system, and the robot arms 21a and 21b holding the medical equipment constitute an operating part on the slave side. When the operator operates the operation handles 11, the movement of one of the robot arms 21a or 21b is controlled so that the distal end portion (the end effector 43 of the surgical instrument 40) of the robot arm 21a or the distal end portion (the endoscope 50) of the robot arm 21b moves following the movement of the operation handles 11.

The patient-side apparatus 20 controls the movement of the robot arms 21a in accordance with the set motion scaling ratio. When the motion scaling ratio is set to ½, for example, the end effectors 43 of the surgical instruments 40 move ½ of the movement distance of the operation handles 11. This allows for precise fine surgery.

The operation pedal section 12 or an operation pedal unit includes plural pedals to execute medical equipment-related functions. The plural pedals include a coagulation pedal, a cutting pedal, a camera pedal, and a clutch pedal. The plural pedals are operated by a foot of the operator.

The coagulation pedal enables the surgical instrument 40 to coagulate a surgery site. Specifically, when the coagulation pedal is operated, voltage for coagulation is applied to the surgical instrument 40 to coagulate the surgery site. The cutting pedal enables the surgical instrument 40 to cut the surgery site. Specifically, the cutting pedal is operated to apply voltage for cutting to the surgical instrument 40 and cut a surgery site.

The camera pedal is used to control the position and orientation of the endoscope 50 that captures images within the body cavity. Specifically, the camera pedal enables operation of the endoscope 50 by the operation handles 11. That is, the position and orientation of the endoscope 50 are controllable by the operation handles 11 while the camera pedal is being pressed. The endoscope 50 is controlled by using both of the right and left operation handles 11, for example. Specifically, when the operator rotates the right and left operation handles 11 about the middle point between the right and left operation handles 11, the endoscope 50 is rotated. When the operator presses the right and left operation handles 11 together, the endoscope 50 goes forward into the body cavity. When the operator pulls the right and left operation handles 11 together, the endoscope 50 goes back. When the operator moves the right and left operation handles 11 together up, down, right, or left, the endoscope 50 moves up, down, right, or left, respectively.

The clutch pedal is used to temporarily disconnect operation-related connection between the operation handles 11 and the robot arms 21a to stop movement of the surgical instruments 40. Specifically, when the clutch pedal is being pressed, the robot arms 21a of the patient-side apparatus 20 do not work even if the operation handles 11 are operated. For example, when the operation handles 11 are operated and moved to the edge of the range of movement, the operator operates the clutch pedal to temporarily disconnect the operation-related connection and then returns the operation handles 11 to the center of the range of movement. When the operator stops operating the clutch pedal, the operation handles 11 are again connected to the robot arms 21a. The operator restarts the operation for the operation handles 11 around the center thereof.

The display 13 (or a display device) is configured to display images captured by the endoscope 50. The display 13 comprises a scope type display or a non-scope type display. (Note that FIG. 1 illustrates a scope type display 13.) The scope type display is a display configured in such a manner that the operator looks into the display. The non-scope type display is a display like an open-type display that includes a flat screen and the operator is able to see without looking into, such as normal displays for personal computers.

When the scope type display is attached, the scope type display displays 3D images captured by the endoscope 50 attached to the robot arm 21b of the patient-side apparatus 20. When the non-scope type display is attached, the non-scope type display also displays 3D images captured by the endoscope 50 provided for the patient-side apparatus 20. The non-scope type display may display 2D images captured by the endoscope 50 provided for the patient-side apparatus 20.

The display 13 is provided with a head sensor 13a for detecting whether or not the operation handle 11 is being operated by the operator. Specifically, the head sensor 13a is configured to detect the presence of the head of the operator. The head sensor 13a is configured to detect whether or not the operator looks into the display 13 to operate the operation handle 11.

As illustrated in FIG. 2, the control apparatus 14 includes a controller 141, a storage 142, and an image controller 143, for example. The controller 141 includes an arithmetic unit such as a CPU. The storage 142 includes a memory, such as a ROM and a RAM. The control apparatus 14 may be composed of a single controller performing centralized control or may be composed of plural controllers that perform decentralized control in cooperation with each other. The controller 141 determines whether an action mode instruction inputted by the operation handles 11 is to be executed by the surgical instruments 40 or to be executed by the endoscope 50, depending on the state of the operation pedal section 12. When determining that the action mode instruction inputted by the operation handles 11 is to be executed by any one of the surgical instruments 40, the controller 141 transmits the action mode instruction to the corresponding robot arm 21a through the controller 24. The robot arm 21*a* is thereby driven by the controller 24 and thus movement of the surgical instrument 40 attached to the robot arm 21*a* is controlled.

When determining that the action mode instruction inputted by the operation handles 11 is to be executed by the endoscope 50, the controller 141 transmits the action mode instruction to the robot arm 21*b* through the controller 24. The robot arm 21*b* is thereby driven for control of movement of the endoscope 50 attached to the robot arm 21*b*.

The storage 142 stores control programs corresponding to the types of the surgical instrument 40, for example. The controller 141 reads the stored control programs according to the types of the attached surgical instruments 40. The action mode instructions from the operation handles 11 and/or the operation pedal section 12 of the remote control apparatus 10 thereby cause the respective surgical instruments 40 to perform proper movements.

The image controller 143 transmits images acquired by the endoscope 50 to the display 13. The image controller 143 performs processing and modifying the images when needed.

(Configurations of Surgical Instrument, Adaptor, Drape, and Robot Arm)

Figure 4:
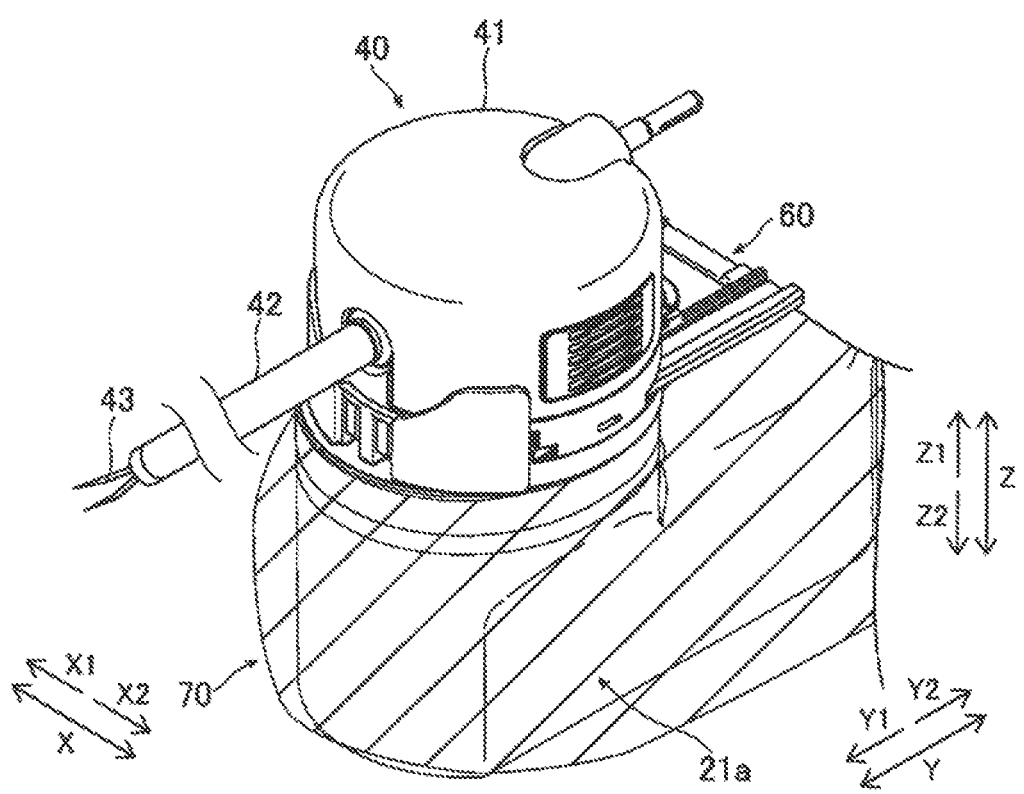
FIG. 4 is a diagram illustrating a perspective view of a state where a surgical instrument is attached to a robot arm through an adaptor according to a first embodiment.
Figure 5:
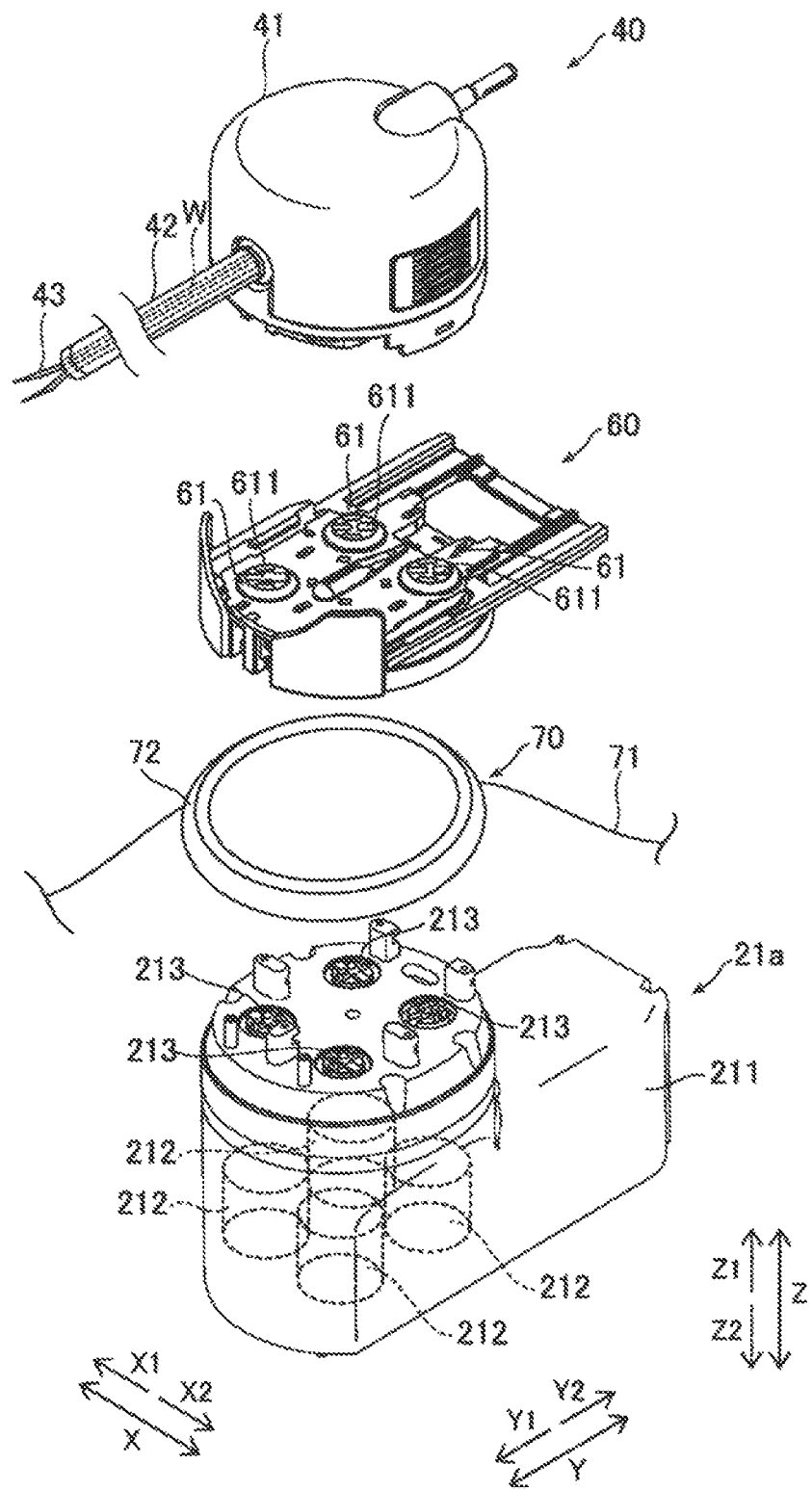
FIG. 5 is a diagram illustrating an exploded perspective view of a state where the surgical instrument is attached to a robot arm through an adaptor according to a first embodiment.
Figure 6:
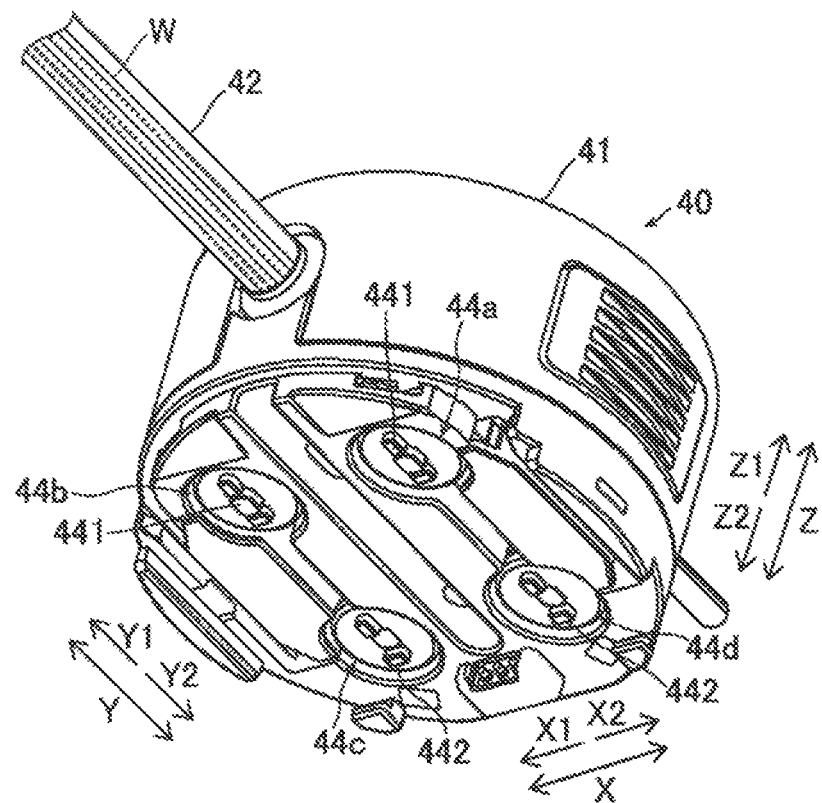
FIG. 6 is a diagram illustrating a perspective view of the surgical instrument according to a first embodiment as seen from below.

With reference to FIGS. 4 to 6, the configurations of the surgical instrument 40, an adaptor 60, a drape 70, and the robot arm 21*a* are described.

Here, the direction in which the surgical instrument 40 (the direction in which the shaft 42 extends) is defined as the Y direction, the distal side (the side toward the end effector 43) of the surgical instrument 40 along the Y direction is defined as the Y1 direction, and the opposite side of the Y1 direction is defined as the Y2 direction. The direction in which the surgical instrument 40 and the adaptor 60 are adjacent to each other is defined as a Z direction, the surgical instrument 40 side along the Z direction is defined as a Z1 direction, and the opposite side of the Z1 direction is defined as a Z2 direction. Further, the direction orthogonal to the Y direction and the Z direction is referred to as an X direction, one side along the X direction is referred as an X1 direction, and the other side along the X direction is referred to as an X2 direction.

As illustrated in FIGS. 4 and 5, the surgical instrument 40 is detachably attached to the robot arm 21*a* of the robotic surgical system 100. Specifically, the surgical instrument 40 is detachably attached to the robot arm 21*a* via the adaptor 60. The adaptor 60 is a drape adaptor configured to sandwich a sterile drape 70 to cover the robot arm 21*a*, in conjunction with the robot arm 21*a*.

The surgical instrument 40 is attached to the Z1 side of the adaptor 60. The adaptor 60 is attached to the Z1 side of the robot arm 21*a*.

The robot arm 21*a* is used in a clean area and is covered with the drape 70. In operation rooms, clean technique is used in order to prevent surgical incision sites and medical equipment from being contaminated by pathogen, foreign matters, or the like. The clean technique defines a clean area and a contaminated area, which is outside the clean area. The surgery sites are located in the clean area. Members of the surgical team, including the operator, make sure that only sterile objects are placed in the clean area during surgery and perform sterilization for an object which is to be moved to the clean area from the contaminated area. Similarly, when an assistant, as one of the members of the surgical team including the operator, places their hands in the contaminated area, the member sterilize their hands before directly touching objects located in the clean area. Instruments used in the clean area are sterilized or are covered with the drapes 70 that are sterilized.

As illustrated in FIG. 5, the drape 70 includes a body section 71 that covers the robot arm 21*a* and an attachment section 72 sandwiched between the robot arm 21*a* and the adaptor 60. The body section 71 is made of a flexible film member. The flexible film member is made of a resin material, such as thermoplastic polyurethane and polyethylene. The body section 71 includes an opening so that the robot arm 21*a* is engaged with the adaptor 60. To the opening of the body section 71, the attachment section 72 is provided. The attachment section 72 is made of a resin mold member. The resin mold member is made of a resin member such as polyethylene terephthalate. The attachment section 72 is harder (less flexible) than the body section 71. The attachment section 72 includes an opening so that the robot arm 21*a* is engaged with the adaptor 60. The opening of the attachment section 72 may be provided corresponding to the section where the robot arm 21*a* is engaged with the adaptor 60. The opening of the attachment section 72 may include plural openings corresponding to plural sections at which the robot arm 21*a* is engaged with the adaptor 60.

As illustrated in FIGS. 5 and 6, the surgical instrument 40 includes plural (four) driven members 44*a*, 44*b*, 44*c*, and 44*d*. The driven members 44*a*, 44*b*, 44*c*, and 44*d* are provided within the housing 41 and are rotatable about the respective rotation axes extending along the Z axis. The plural driven members 44*a* to 44*d* are provided to operate (drive) the end effector 43. The driven members 44*a*, 44*b*, 44*c*, and 44*d* are connected to the end effector 43 via soft elongate elements W (such as wires or cables) passing through the inside of the shaft 42. With this, rotations of the driven members 44*b* to 44*d* drive the elongate element W, which operate (drive) the end effector 43. In addition, the driven member 44*a* is connected to the shaft 42 through gears 42*a* (see FIG. 7). With this, the shaft 42 is rotated with rotation of the driven member 44*a*, and the end effector 43 is rotated with rotation of the shaft 42.

To transmit driving forces from the robot arm 21*a* to the end effector 43, each of the driven members 44*a* to 44*d* includes a projection 441 or 442, which is engaged with the corresponding drive transmission member 61 of the adaptor 60. Each of the projections 441 and 442 is projected from the Z2 side surface of the corresponding driven member 44*a*, 44*b*, 44*c*, or 44*d* toward the side of the adaptor 60 (the Z2 side). Each of the projections 441 and 442 includes plural projection portions that arranged in a straight line. The protrusions 441 provided to the driven members 44*a* and 44*b* have different shapes from that of the protrusions 442 provided to the driven members 44*c* and 44*d*.

As illustrated in FIG. 5, the adaptor 60 includes a plurality (four) of the drive transmission members 61. The drive transmission members 61 are configured to transmit the driving forces from the robot arm 21*a* to the driven members 44*a* to 44*d* of the surgical instrument 40. That is, the drive transmission members 61 are provided so as to correspond to the driven members 44*a* to 44*d* of the surgical instrument 40. The drive transmission members 61 are rotatable about the respective rotation axes, which extend along the Z direction.

Each of the drive transmission members 61 includes an engagement recess 611 which is engaged with the projection 441 or 442 of the corresponding driven members 44*a*, 44*b*, 44*c*, and 44*d* of the surgical instrument 40. The engagement recess 611 is located at the surgical instrument 40 side (the Z1 side) of the drive transmission member 61 and is recessed from the Z1 side surface of the drive transmission member 61, toward the Z2 direction, opposite to the surgical instrument 40. Each of the drive transmission members 61 includes an engagement recess, which is provided on the Z2 side surface thereof and is configured to be engaged with a corresponding one of engagement projections 213 of the robot arm 21a.

The robot arm 21a includes a frame 211, plural (four) drive parts 212, and the plural engagement projections 213. The plural drive part 212 are provided corresponding to the plural (four) driven members 44a to 44d of the surgical instrument 40 and corresponding to the plural (four) drive transmission members 61 of the adaptor 60. Each of the drive parts 212 includes an absolute encoder and a servomotor and is configured to drive the engagement projection 213 to rotate about the rotational axes thereof extending in the Z direction. The engagement projection 213 is engaged with the engagement recess provided on the Z2 side surface of the corresponding drive transmission member 61. The engagement projection 213 is projected from the Z1 side surface of the robot arm 21a toward the Z1 side (the adaptor 60 side). The drive parts 212 are configured to drive the drive transmission members 61 of the adaptor 60, engaged with the engagement projections 213 of the drive parts 212, to rotate about the rotational axes B of the drive transmission members 61 extending in the Z direction, so as to drive the driven members 44a to 44d of the surgical instrument 40, engaged with the drive transmission members 61, to rotate about the rotational axes of the driven members 44a to 44d extending in the Z direction.

(Detailed Configuration of Surgical Instrument)

Figure 7:
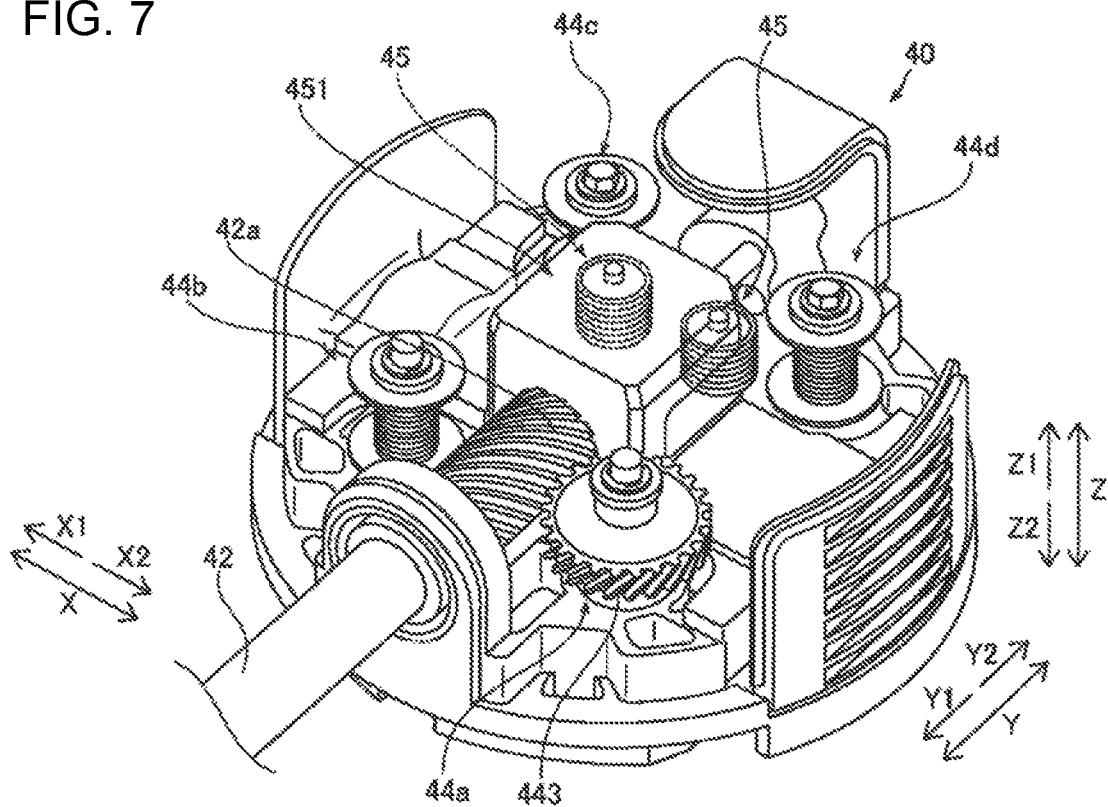
FIG. 7 is a diagram illustrating a perspective view of a state where a cover part is detached from a base part of the surgical instrument according to a first embodiment.
Figure 8:
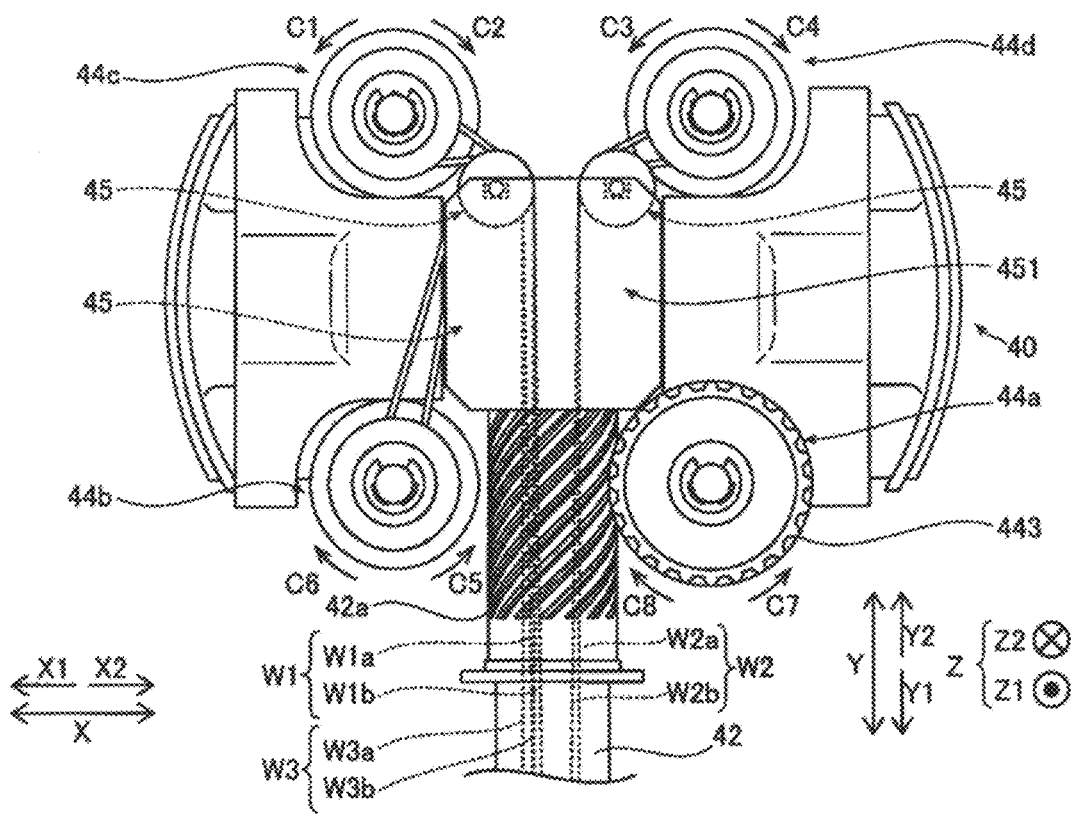
FIG. 8 is a diagram illustrating a plan view of a state where a cover part is detached from a base part of the surgical instrument according to a first embodiment.

With reference to FIGS. 7 to 9, the configuration of the surgical instrument 40 is described in detail below. Here, the case is described below in which the end effector 43 of the surgical instrument 40 is a grasping forceps including the pair of jaw members 43a and 43b.

As illustrated in FIGS. 7 and 8, the elongate elements W are wound around the driven members 44b to 44d of the surgical instrument 40. That is, the elongate elements W are connected to the driven members 44b to 44d.

The elongate element W3 is wound around the driven member 44b of the surgical instrument 40. Specifically, a first portion W3a of the elongate element W3 is wound clockwise around an upper portion of the driven member 44b, and a second portion W3b of the elongate element W3 is wound counterclockwise around a lower portion of the driven member 44b.

The elongate element W1 is wound around the driven member 44c of the surgical instrument 40. Specifically, a first portion W1a of the elongate element W1 is wound clockwise around an upper portion of the driven member 44c, and a second portion W1b of the elongate element W1 is wound counterclockwise around a lower portion of the driven member 44c.

The elongate element W2 is wound around the driven member 44d of the surgical instrument 40. Specifically, a first portion W2a of the elongate element W2 is wound clockwise around an upper portion of the driven member 44d, and a second portion W2b of the elongate element W2 is wound counterclockwise around a lower portion of the driven member 44d.

The elongate elements W extend from the driven members 44b to 44d through the shaft 42 to the end effector 43, are wound around the end effector 43, return to the driven members 44b to 44d through the shaft 42. Further, the elongate elements W are wound around built-in pulleys 45 in the housing 41, respectively. The built-in pulleys 45 are retained by a pulley retainer 451.

Figure 9A:
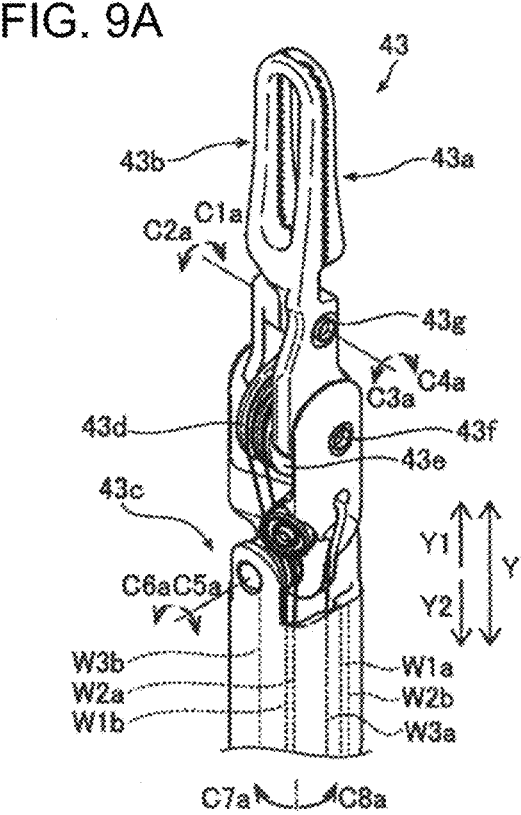
FIGS. 9A and 9B are diagrams illustrating perspective views of an end effector of the surgical instrument according to a first embodiment.
Figure 9B:
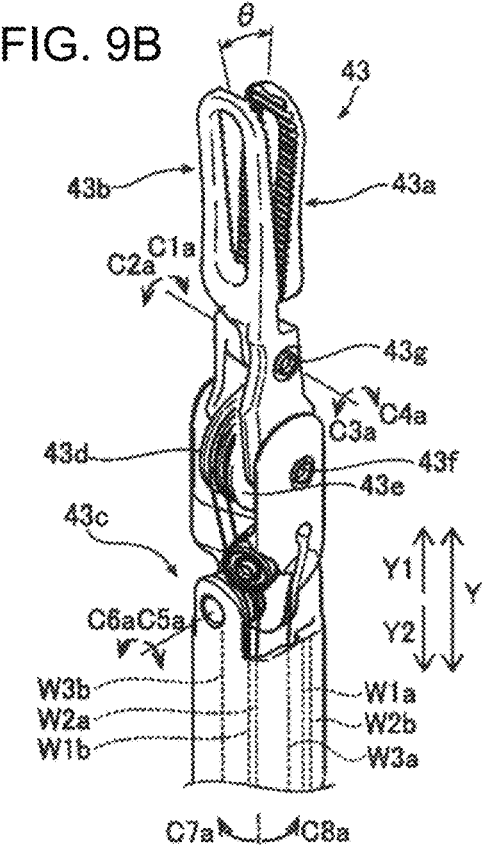

As illustrated in FIGS. 8 and 9, when the driven member 44c rotates about the rotary axis thereof, the rotation of the driven member 44c operates the jaw member 43a, which is one of the pair of jaw members 43a and 43b of the end effector 43. Specifically, the driven member 44c is rotated by the drive part 212 to drive the elongate element W1. The elongate element W1 extends through the inside of the shaft 42 and connects the jaw member 43a and the driven member 44c. When the driven member 44c is rotated in the C1 direction (see FIG. 8), the first portion W1a of the elongate element W1 is pulled and the second portion W1b of the elongate element W1 is fed, so as to drive the jaw member 43a to move in the C1a direction (see FIGS. 9A and 9B), which is a direction to open the jaw member 43a. When the driven member 44c is rotated in the C2 direction (see FIG. 8) opposite to the C1 direction, the first portion W1a of the elongate element W1 is fed and the second portion W1b of the elongate element W1 is pulled, so as to drive the jaw member 43a to move in the C2a direction (see FIGS. 9A and 9B), which is a direction to close the jaw member 43a.

When the driven member 44d rotates about the rotary axis thereof, the rotation of the driven member 44d operates the jaw member 43b, which is one of the pair of jaw members 43a and 43b of the end effector 43. Specifically, the driven member 44d is rotated by the drive part 212 to drive the elongate element W2. The elongate element W2 extends through the inside of the shaft 42 and connects the jaw member 43b and the driven member 44d. When the driven member 44d is rotated in the C3 direction (see FIG. 8), the first portion W2a of the elongate element W2 is pulled and the second portion W2b of the elongate element W2 is fed, so as to drive the jaw member 43b to move in the C3a direction (see FIGS. 9A and 9B), which is a direction to open the jaw member 43b. When the driven member 44d is rotated in the C4 direction (see FIG. 8) opposite to the C3 direction, the first portion W2a of the elongate element W2 is fed and the second portion W2b of the elongate element W2 is pulled, so as to drive the jaw member 43b to move in the C4a direction (see FIGS. 9A and 9B), which is a direction to close the jaw member 43b. That is, the pair of jaw members 43a and 43b are opened and closed with respect to each other by the movements of the elongate elements W driven by the driven members 44b and 44c.

By being rotated about the rotation axis thereof, the driven member 44b operates a wrist portion 43c of the end effector 43. Specifically, the driven member 44b is rotated by the drive part 212 to drive the elongate element W3. The elongate element W3 extends through the inside of the shaft 42 and connects the wrist portion 43c and the driven member 44b. When the driven member 44b is rotated in the C5 direction (see FIG. 8), the first portion W3a of the elongate element W3 is pulled and the second portion W3b of the elongate element W3 is advanced, so as to drive the wrist portion 43c to move in the C5a direction (see FIGS. 9A and 9B). When the driven member 44d is rotated in the C6 direction (see FIG. 8) opposite to the C5 direction, the second portion W3b of the elongate element W3 is pulled and the first portion W3a of the elongate element W3 is fed, so as to drive the wrist portion 43c to move in the C6a direction (see FIGS. 9A and 9B), which is opposite to the C5a direction.

When the drive part 212 rotates the driven member 44a about the rotation axis thereof with the gear portion 443 of the driven member 44a being engaged with a gear portion 42a connected to the proximal end of the shaft 42, the shaft 42 is driven to operate the end effector 43. Specifically, when the driven member 44a rotates in the C7 direction (see FIG. 8), the shaft 42 is driven to rotate in the C7a direction (see FIGS. 9A and 9B) and thus the end effector 43 is driven to rotate in the C7a. When the driven member 44a rotates in the C8 direction (see FIG. 8), the shaft 42 is driven to rotate in the C8a direction (see FIGS. 9A and 9B), which is opposite to the C7a direction, and thus the end effector 43 is driven to rotate in the C8a direction.

(Control of Opening and Closing Pair of Jaw Members)

Next, a control of opening and closing the pair of jaw members 43a and 43b is described with reference to FIGS. 11 to 14. In the following, the drive part 212 of the robot arm 21a that drives the jaw member 43a is referred to as a drive part 212a, and the drive part 212 of the robot arm 21a that drives the jaw member 43b is referred to as a drive part 212b.

Figure 11:
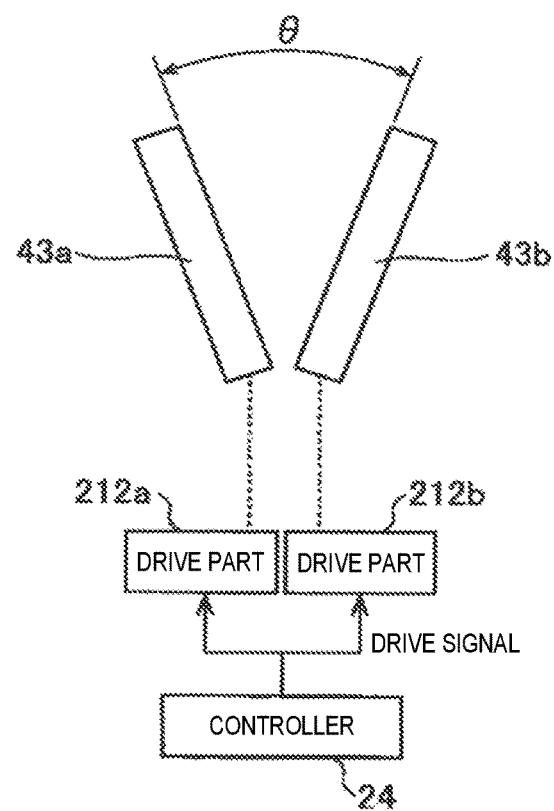
FIG. 11 is a diagram illustrating the pair of jaw members, drive parts, and a controller according to a first embodiment.
Figure 12:
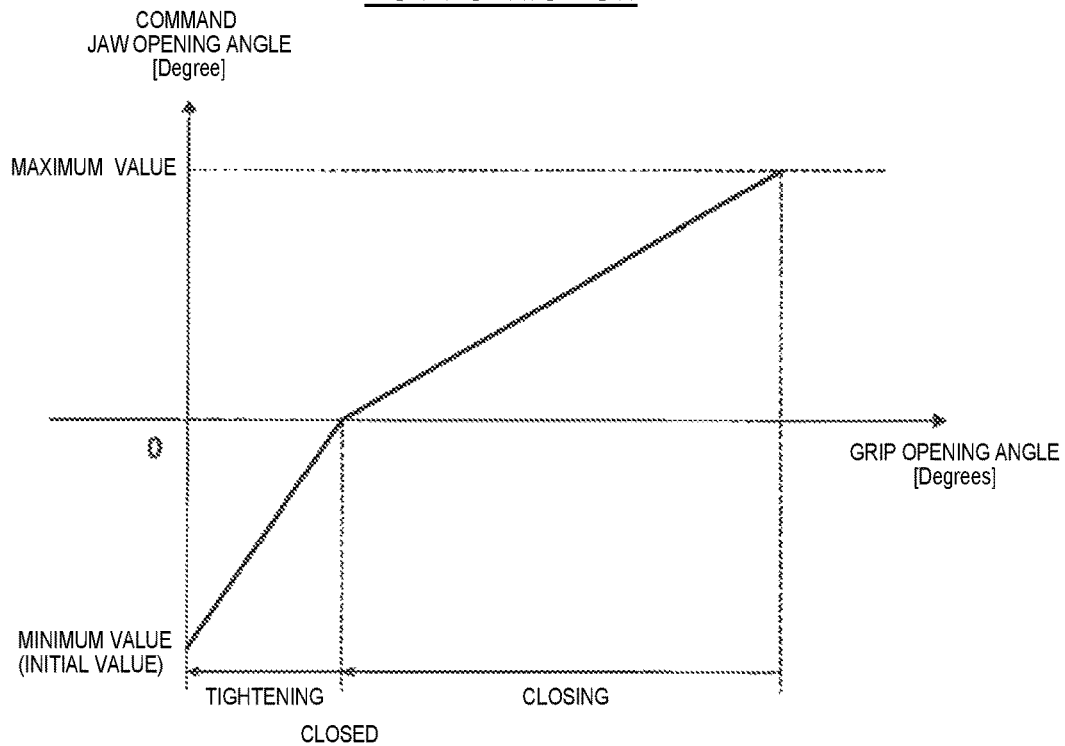
FIG. 12 is a graph illustrating a relationship between a grip opening angle of the operation handle and a command jaw opening angle when there is no restriction according to a first embodiment.

As illustrated in FIGS. 11 and 12, the controller 24 included in the patient-side apparatus 20 is configured, based on a command jaw opening angle (or a command angle) for the opening angle θ of the pair of jaw members 43a and 43b, to drive the motors of the drive part 212a and 212b to rotate. The command jaw opening angle is a command value of the opening angle θ between the pair of jaw members 43a and 43b, and is associated with (is generated based on) the input of the operation handle 11. The command jaw opening angle is converted by the controller 24 into a command value (a drive signal) to rotate the motors of the drive parts 212a and 212b by rotation amounts thereof so as to make the opening angle θ between the pair of jaw members 43a and 43b corresponded to the opening angle between the pair of grip members 11b of the operation handle 11.

FIG. 12 is a graph illustrating a relationship between the opening angle between the pair of grip members 11b of the operation handle 11 and the command jaw opening angle for the opening angle between the pair of jaw members 43a and 43b in a mode other than a restriction mode described later). In the graph illustrated in FIG. 12 (and FIG. 13), the horizontal axis indicates the opening angle between the pair of grip members 11b, and the vertical axis indicates the command jaw opening angle for the opening angle between the pair of jaw members 43a and 43b. The graph of FIG. 12 indicates that, as the opening angle between the pair of grip members 11b becomes smaller, the pair of jaw members 43a and 43b gradually close. The graph of FIG. 12 also indicates that when the motors of the drive parts 212a and 212b are energized to try to rotate the pair of jaw members 43a and 43b in the closing direction thereof after the pair of jaw members 43a, 43b are completely closed (that is, after the opening angle θ becomes zero), a tightening force (a grasping force) is generated between the pair of jaw members 43a and 43b.

Here, regardless of whether or not the object T (see FIG. 14) exists between the pair of jaw members 43a and 43b, if the pair of jaw members 43a and 43b can be tightened up to a minimum value of the command jaw opening angle illustrated in the graph of FIG. 12, an excessive grasping force may occur.

Figure 13:
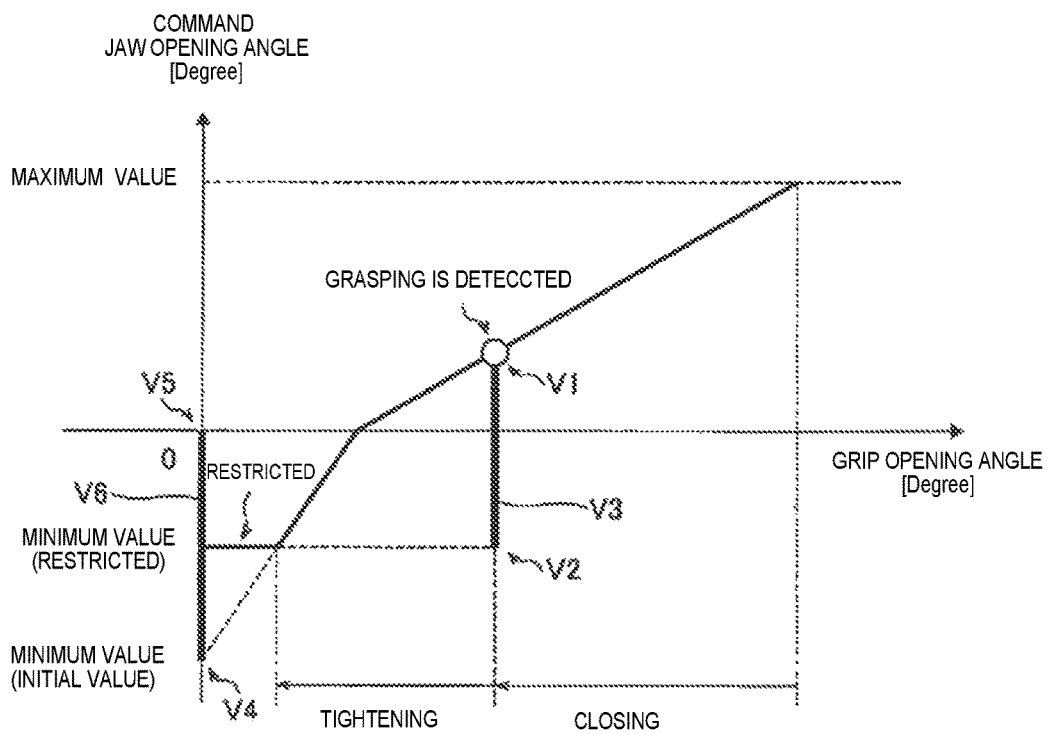
FIG. 13 is a graph illustrating a relationship between the grip opening angle of the operation handle and the command jaw opening angle in the restriction mode according to a first embodiment.
Figure 14:
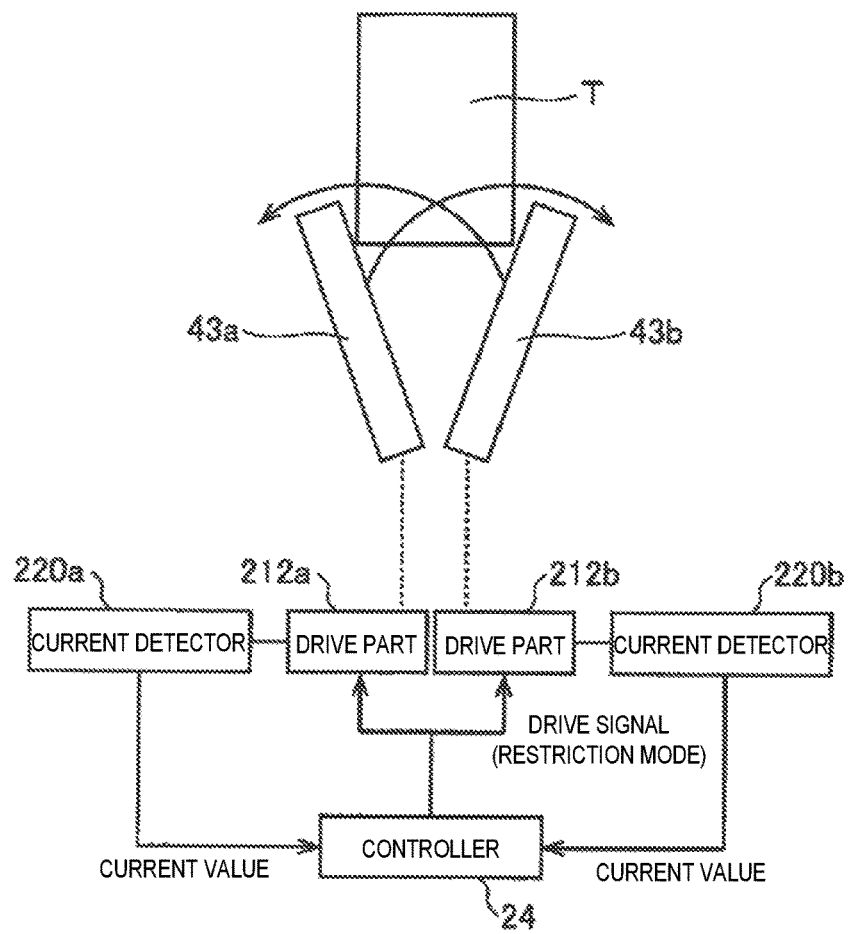
FIG. 14 is a diagram illustrating an explanatory view for explaining grasping an object by the pair of jaw members according to a first embodiment.

In light of this, in a first embodiment, as illustrated in FIGS. 13 and 14, the controller 24 is configured to monitor current values (hereinafter, motor current values) applied to the motors of the drive parts 212a and 212b during the closing operation of the pair of jaw members 43a and 43b, and to, when it is determined based on the motor current values that the object T is being grasped, drive the drive parts 212a and 212b in the restriction mode in which a magnitude of the command jaw opening angle is restricted. That is, the controller 24 is configured to determine whether or not the motor current value of the drive part 212a or 212b exceeds a predetermined threshold value during the closing operation of the pair of jaw members 43a and 43b, and when it is determined that the motor current value of the drive part 212a or 212b exceeds the predetermined threshold value, to drive the drive parts 212a and 212b in the restriction mode, in which the magnitude of the command jaw opening angle is restricted. Accordingly, when it is determined that the motor current value of the drive part 212a or 212b exceeds the predetermined threshold value during the closing operation of the pair of jaw members 43a and 43b, the drive parts 212a and 212b are driven in the restriction mode in which the magnitude of the command jaw opening angle is restricted. Therefore, it is possible to prevent the grasping force from becoming excessive. As a result, an appropriate grasping force can be obtained. Further, since the magnitude of the command jaw opening angle is restricted, it is not necessary to provide load cells or torque sensors to the elongate elements W. Therefore, it is possible to make the structure around the elongate elements W less complicated than a case where the load cells or the torque sensors are provided to the elongate elements W. As a result, it is possible to achieve an appropriate grasping force while suppressing the structure around the elongate elements W from being complicated.

Specifically, the controller 24 is configured, upon determining that the motor current value of the drive part 212a or 212b exceeds the predetermined threshold value during the closing operation of the pair of jaw members 43a and 43b, to drive the drive parts 212a and 212b in the restriction mode in which a minimum value V2 (a lower limit V2) of the command jaw opening angle in the restriction mode is set (restricted) greater than an initial value, which is a minimum value V4 (a lower limit V4) of the command jaw opening angle in a mode other than the restriction mode, in such a manner that a difference between the minimum value V2 of the command jaw opening angle in the restriction mode and the value V1 of the command jaw opening angle when the motor current value of the drive part 212a or 212b exceeds the predetermined threshold value is a predetermined value V3. That is, the drive parts 212a and 212b are driven in the restriction mode in which the minimum value V2 of the command jaw opening angle is set (restricted) greater than the minimum value V4 of the command jaw opening angle in the mode other than the restriction mode. Therefore, it is possible to easily prevent the grasping force from becoming excessive. As a result, an appropriate grasping force can be achieved more easily.

In other words, the controller 24 is configured, in response to determining that the motor current value of the drive part 212a or 212b exceeds the predetermined threshold value, to reset the minimum value (the initial value V4) of the command jaw opening angle to the value (e.g., V2) greater than the initial value V4, in such a manner that a closing angle of the jaw members 43a and 43b from a time when it is determined that the motor current value of the drive part 212a or 212b exceeds the predetermined threshold value is set to the predetermined value V3 (constant value).

In the restriction mode, when it is determined that the value of the command jaw opening angle generated corresponding to the opening angle between the pair of grip members 11b of the operation handle 11 is less than the minimum value V2 of the command jaw opening angle in the restriction mode (the restricted minimum value V2), the controller 24 is configured to drive the drive parts 212a and 212b in accordance with the command jaw opening angle that is set (restricted) to the minimum value V2 of the command jaw opening angle in the restriction mode (the restricted minimum value V2). Further, in the restriction mode, when it is determined that the value of the command jaw opening angle generated corresponding to the opening angle between the pair of grip members 11b of the operation handle 11 is equal to or greater than the minimum value V2 of the command jaw opening angle in the restriction mode (the restricted minimum value V2), the controller 24 is configured to drive the drive parts 212a and 212b in response to the value of the command jaw opening angle generated corresponding to the opening angle between the pair of grip members 11b of the operation handle 11 in a same manner as in the mode (FIG. 12) other than the restriction mode.

Further, in a first embodiment, the predetermined value V3, which is the difference between the value V1 of the command jaw opening angle when the motor current value of the drive part 212a or 212b exceeds the predetermined threshold value and the minimum value V2 of command jaw opening angle in the restriction mode, is set to the same as a difference V6 between the value V5 of the command jaw opening angle when the opening angle θ of the pair of jaw members 43a and 43b is zero and the initial minimum value V4, which is the minimum value V4 of the command jaw opening angle in the mode other than the restriction mode. As a result, the drive parts 212a and 212b can be driven in the restriction mode in which the minimum value of the command jaw opening angle is restricted in such a manner that the difference between the value V1 of the command jaw opening angle when the motor current values of the drive part 212a or 212b exceeds the predetermined threshold value and the minimum value V2 of the command jaw opening angle in the restriction mode is set to the same as the difference V6 between the value V5 of the command jaw opening angle when the opening angle θ of the pair of jaw members 43a and 43b is zero and the initial minimum value V4 of the command jaw opening angle. As a result, in the restriction mode, it is possible to generate a constant grasping force substantially corresponding to a maximum grasping force when the pair of jaw members 43a and 43b do not grasp the object T. Therefore, it is possible to more easily prevent an excessive grasping force from being generated. As a result, an appropriate grasping force can be achieved more easily.

Further, in a first embodiment, the controller 24 is configured to switch to the restriction mode, when it is determined that the motor current value of the drive part 212a or 212b exceeds the predetermined threshold value, and the value of the command jaw opening angle generated is smaller than the previous value of the command jaw opening angle (the value immediately before), which is stored in the memory 25 in the patient-side apparatus 20 (see FIG. 1). The memory 25 stores therein the value of the command jaw opening angle at predetermined time intervals. Accordingly, when it is detected, based on the motor current values of the drive parts 212a and 212b, that the pair of jaw members 43a and 43b are grasping the object T and it is detected, based on the value of the command jaw opening angle generated becoming smaller than the previous value of the command jaw opening angle, that the pair of jaw members 43a and 43b are closing, the controller switches to restriction mode. As a result, it is possible to switch to the restriction mode at an appropriate timing when the grasping force of the pair of jaw members 43a and 43b should be restricted. Note that the memory 25 is an example of a storage or a storage device.

Specifically, the controller 24 is configured to switch to the restriction mode, when it is repeatedly determined multiple times (for example, two times) that the motor current value of the drive part 212a or 212b exceeds the predetermined threshold value and the value of the command jaw opening angle generated gets smaller than the previous value of the command jaw opening angle stored immediately before in the memory 25. Accordingly, the controller 24 can switch to the restriction mode, when it is detected with certainty that the pair of jaw members 43a and 43b are grasping the object T based on the motor current values of the drive parts 212a and 212b and that the pair of jaw members 43a and 43b are closing based on the value of the command jaw opening angle generated getting smaller than the previous value of the command jaw opening angle. As a result, it is possible to switch to the restriction mode at a more appropriate timing.

More specifically, the controller 24 is configured to switch to the restriction mode, when it is repeatedly determined multiple times that one of the motor current value of the drive part 212a and the motor current value of the drive part 212b exceeds the predetermined threshold value and that the value of the command jaw opening angle gets smaller than the previous value of the command jaw opening angle stored immediately before in the memory 25.

Further, in a first embodiment, the controller 24 is configured, when the motor current value of the drive part 212a or 212b gets equal to or less than the predetermined threshold value, to release (finish) the restriction mode. Thereby, when it is detected based on the motor current values of the drive parts 212a and 212b that the grasping of the object T by the pair of jaw members 43a and 43b is released, the restriction mode is released (ended). As a result, the restriction mode can be released at an appropriate timing when the restriction mode should be released.

Specifically, in a state where the surgical instrument 40 is operable (is allowed to be operated) by the operation handle 11, the controller 24 is configured to release the restriction mode, when it is detected that the motor current value of the drive part 212a or 212b gets equal to or less than the predetermined threshold value and it is detected that the value of the command jaw opening angle generated exceeds the value of the command jaw opening angle at the start of the restriction mode (that is, V1) or a value close to the maximum value of the command jaw opening angle (for example, a value one degree smaller than the maximum value). Further, in the state where the surgical instrument 40 is operable by the operation handle 11, the controller 24 can release the restriction mode, when it is detected, based on the motor current value of the drive part 212a or 212b, that the grasping of the object T by the pair of jaw members 43a and 43b is released and it is detected, based on the value of the command jaw opening angle exceeding the value of the command jaw opening angle at the start of the restriction mode, that the pair of jaw members 43a and 43b are opened more than the jaw opening angle at the start of the restriction mode. As a result, the restriction mode can be released (ended) at a more appropriate timing. Further, when it is detected, based on the motor current values of the drive parts 212a and 212b, that grasping of the object T by the pair of jaw members 43a and 43b is released and it is detected, based on the value of the command jaw opening angle exceeding the value close to the maximum value of the command jaw opening angle (an approximate maximum value of the command jaw opening angle or a value slightly smaller than the maximum value), that the pair of jaw members 43a and 43b are in a maximum open state, the controller can release the restriction mode. As a result, even in a case where the pair of jaw members 43a and 43b have been opened to the maximum at the start of the restriction mode and thus the pair of jaw members 43a and 43b cannot be opened more from the state at the start of the restriction mode, the restriction mode can be released.

Note that the controller 24 is configured, when the head sensor 13a (see FIG. 1) detects the presence of the operator's head and the operator performs a predetermined operation using the operation handle 11, to determine (detect) that the surgical instrument 40 is in an operable state (hereinafter, may be referred to as a following state) in which the surgical instrument 40 can be operated by the operation handle 11. Further, the controller 24 is configured, when the head sensor 13a detects no presence of the operator's head, to determine (detect) that the surgical instrument 40 is in an inoperable state (hereinafter, may be referred to as an out-of-following state or a no-following state) in which the surgical instrument 40 is not allowed to be operated by the operation handle 11.

Further, in a first embodiment, in the out-of-following state, the controller 24 is configured, when it is detected that the motor current value of the drive part 212a, 212b gets equal to or less than the predetermined threshold value, to release (end) the restriction mode regardless of the value of the command jaw opening angle, with considering that the command jaw opening angle does not change in the out-of-following state. Accordingly, when it is detected, based on the motor current value of the drive part 212a, 212b, that grasping of the object by the pair of jaw members 43a and 43b is released in the out-of-following state, the restriction mode can be released regardless of the value of the command jaw opening angle. As a result, the restriction mode can be released under the condition suitable for the out-of-following state. Note that after starting the restriction mode in the following state, the following state may be switched to the out-of-following state and the restriction mode may be continued in the out-of-following state. In this case, if the above conditions are satisfied, the restriction mode is released.

Further, in a first embodiment, the predetermined threshold value is set based on frictional forces of the motors of the drive parts 212a and 212b. With this, the predetermined threshold value for detecting whether the pair of jaw members 43a and 43b grasp an object T can be set in consideration of the influence of the current values generated due to the frictional forces of the drive parts 212a and 212b. As a result, it is possible to accurately detect based on the predetermined threshold value whether the pair of jaw members 43a and 43b is grasping an object T, as compared with a case where the influence of the current values generated due to the frictional forces of the drive parts 212a and 212b is not taken into consideration.

Specifically, the predetermined threshold value may be set by a following equation (1). As expressed in the equation (1) below, the predetermined threshold value is set in consideration of a dynamic friction of the motor of the drive part 212a (212b) and a product of a viscous friction of the motor of the drive part 212a (212b) and an axial speed (rotational speed) of the drive part 212a (212b), with respect to a reference value. Since the current value that is generated due to the viscous friction of the drive part 212a (212b) varies according to the axial speed of the drive part 212a (212b), the current value is considered as a value that varies according to the axial speed of the drive part 212a (212b) in the equation (1). Further, since the current value that is generated due to the dynamic friction of the drive part 212a (212b) is constant regardless of the axial speed of the drive part 212a (212b), the current value is considered as a constant value that does not vary according to the axial speed of the drive part 212a (212b) in the equation (1).

$$\alpha = \alpha1 + (a \times As + b) \quad (1)$$

α: the predetermined threshold value
α1: the reference value
a: a constant related to the viscous friction of the drive part
b: a constant related to the dynamic friction of the drive part
As: a variable of the axial speed (rotational speed) of the drive part "α1" is a constant that serves as a reference for the predetermined threshold value. "a" is a constant related to the viscous friction generated due to grease or the like in a speed reducer or the like of the drive part 212a (212b). "b" is a constant related to the dynamic friction generated due to the rotation in the speed reducer or the like of the drive part 212a (212b). The constants "α1", "a" and "b" have been obtained in advance by experiments and the like. The constants "α1", "a" and "b" are not particularly limited. However, as an example, "α1" is 0.2 (Arms), "a" is 0.0006 (Arms/sec/deg), and "b" is 0.1194 (Arms). "As" is a variable representing the axial speed (rotational speed) of the drive part 212a (212b). "As" can be acquired based on an output of the position detector such as the encoder of the drive part 212a (212b).

The controller 24 is configured, when determining whether or not to switch to the restriction mode, to compare the predetermined threshold value of the drive part 212a that is obtained on the real time based on the equation (1) with the motor current value of the drive part 212a that is obtained on the real time from the current detector 220a that is provided for the drive part 212a and configured to detect the motor current value of the drive part 212a. Likewise, the controller 24 is configured, when determining whether or not to switch to the restriction mode, to compare the predetermined threshold value of the drive part 212b that is obtained on the real time based on the equation (1) with the motor current value of the drive part 212b that is obtained on the real time from the current detector 220b that is provided for the drive part 212b and is configured to detect the motor current value of the drive part 212b.

Figure 10:
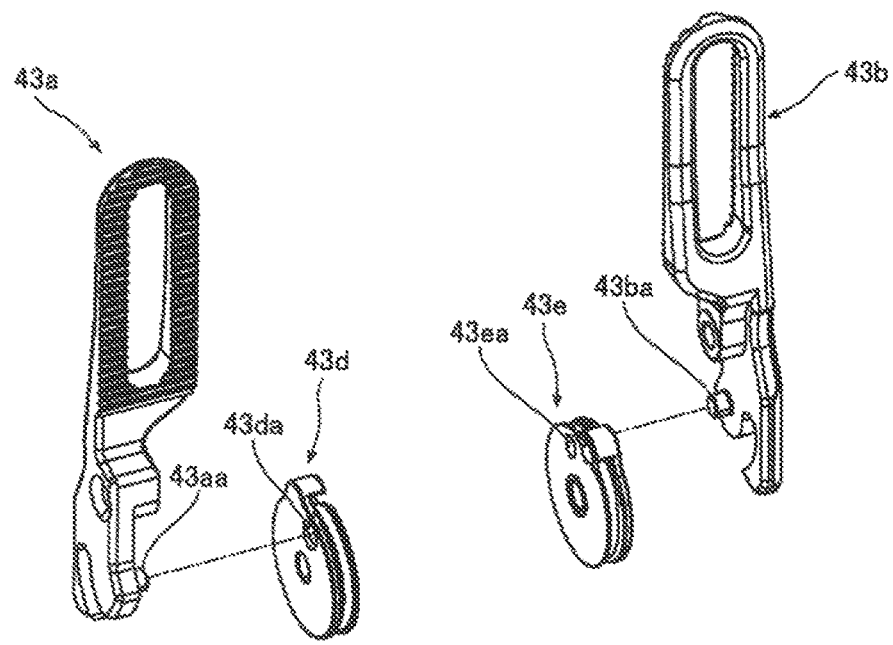
FIG. 10 is an exploded perspective view illustrating a pair of jaw members and pulleys of the end effector according to a first embodiment.

Further, in a first embodiment, as illustrated in FIGS. 9 and 10, the end effector 43 includes a pulley 43d around which the elongate element W1 for driving the jaw member 43a is wound, and a pulley 43e around which the elongate element W2 for driving the jaw member 43b is wound. The pulley 43d is provided with an engagement hole 43da that engages with an engagement pin 43aa of the jaw member 43a, and the pulley 43e is provided with an engagement hole 43ea that engages with an engagement pin 43ba of the jaw member 43b. The pair of jaw members 43a and 43b are configured, when the pulleys 43d and 43e are rotated, to open and close with respect to each other about a shaft 43g (including a rotational axis) different from a shaft 43f (including a rotational axis) of the pulleys 43d and 43e. That is, the pair of jaw members 43a and 43b and the pulleys 43d and 43e form a link mechanism. As a result, it is possible to generate a large grasping force by the pair of jaw members 43a and 43b. Further, in the case where the pair of jaw members 43a and 43b are used that have a large grasping force, it is possible to suppress generation of an excessive grasping force by using the restriction mode described above. Note that the engagement hole 43*da* and the engagement hole 43*ea* are examples of engagement portions for driving the jaw member.

The elongate element W1 is wound around the pulley 43*d*, so that the pulley 43*d* is rotated by movements of the elongate element W1. The elongate element W2 is wound around the pulley 43*e*, so that the pulley 43*e* is rotated by movements of the elongate element W2. The pulley 43*d* and 43*e* are rotatably supported by the common shaft 43*f*. The pair of jaw members 43*a* and 43*b* are rotatably supported by the common shaft 43*g*. The shaft 43*f* and the shaft 43*g* extend substantially parallel to each other. The shaft 43*g* is arranged between the distal end side portion and the proximal end side portion of the pair of jaw members 43*a* and 43*b*. The shaft 43*g* is arranged between the pulleys 43*d* and 43*e* and the distal end side portion of the pair of jaw members 43*a* and 43*b*. The proximal end side portion of the jaw member 43*a* is provided with the engagement pin 43*aa* to be inserted into the engagement hole 43*da* of the pulley 43*d*. The proximal end side portion of the jaw member 43*b* is provided with the engagement pin 43*ba* to be inserted into the engagement hole 43*ea* of the pulley 43*e*.

When the pulley 43*d* is rotated around the shaft 43*f* by the elongate element W1, the rotational driving force is transmitted to the jaw member 43*a* via the engagement pin 43*aa* engaged with the engagement hole 43*da*. With this, the jaw member 43*a* is rotated about the shaft 43*g*. At this time, the rotational driving force of the pulley 43*d* is amplified by the action of the link mechanism and transmitted to a grasping portion of the jaw member 43*a* provided at the distal end side portion of the jaw member 43*a*. Similarly, when the pulley 43*e* is rotated around the shaft 43*g* by the elongate element W2, the rotational driving force is transmitted to the jaw member 43*b* via the engagement pin 43*ba* engaged with the engagement hole 43*ea*. With this, the jaw member 43*b* is rotated around the shaft 43*g*. At this time, the rotational driving force of the pulley 43*e* is amplified by the action of the link mechanism and transmitted to a grasping portion of the jaw member 43*b* provided at the distal end side portion of the jaw member 43*b*.

Here, in a case where a relatively large object T (see FIG. 14) is grasped by the pair of jaw members 43*a* and 43*b* that can generate the large grasping force as illustrated in FIGS. 9A and 9B, an excessive grasping force is likely to be generated. If the excessive grasping force is generated, the elongate elements W1 and W2 may fall off from the built-in pulleys 45 (see FIG. 8). That is, when the excessive grasping force is generated, for example, one of the first portion W1*a* and the second portion W1*b* of the elongated element W1 that is fed out is excessively fed out, so that the elongate element W1 may be loosened around the built-in pulley 45 and may be fall off from the built-in pulley 45. Note that the same may happen for the elongate element W2.

Figure 15:
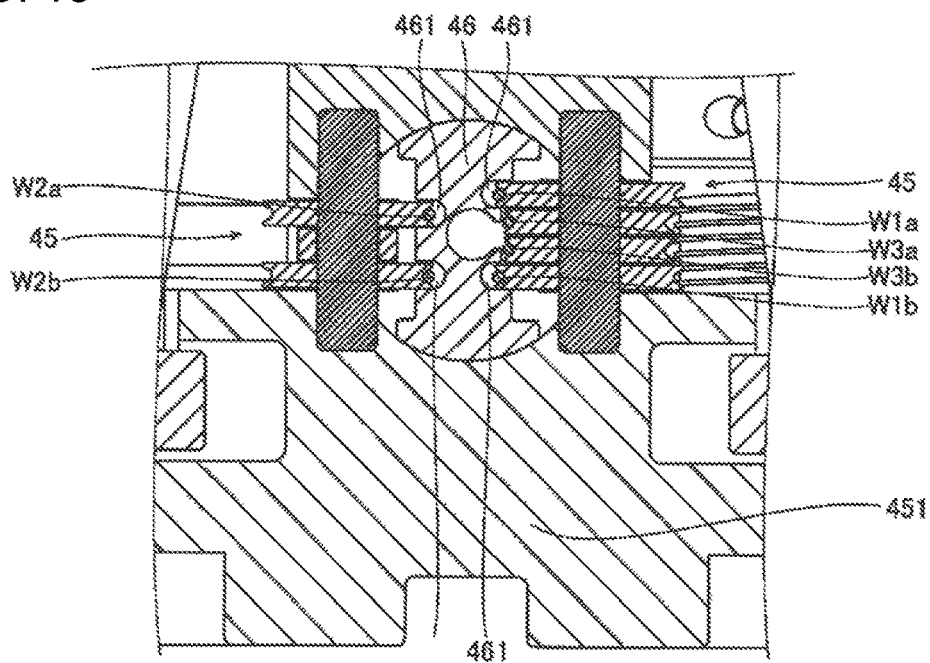
FIG. 15 is a diagram of a cross-sectional view illustrating the elongate elements, pulleys, and a fall-off prevention part according to a first embodiment.

Therefore, in a first embodiment, as illustrated in FIG. 15, a fall-off prevention part 46 configured to prevent the elongate elements W1 and W2 from falling off from the built-in pulleys 45 is provided in the vicinity of the built-in pulleys 45. The fall-off prevention part 46 includes recesses 461 configured to retain the elongate elements W1 and W2 between the recesses 461 and groove portions of the built-in pulleys 45. The recesses 461 cover the groove portions of the built-in pulleys 45 from the side, so that the elongate elements W1 and W2 positioned in the groove portions of the built-in pulleys 45 are retained in the spaces between the groove portions of the built-in pulleys 45 and the recesses 461. Further, the number of the recesses 461 is four corresponding to a total of four portions of the elongate elements W1 and W2, which includes the first portion W1*a* and the second portion W1*b* of the elongate element W1 and the first portion W2*a* and the second portion W2*b* of the elongate element W2.

(Control Process of Starting Restriction Mode)

Next, with reference to the flowchart of FIG. 16, a control process for starting the restriction mode by the controller 24 in the following state is described below.

Figure 16:
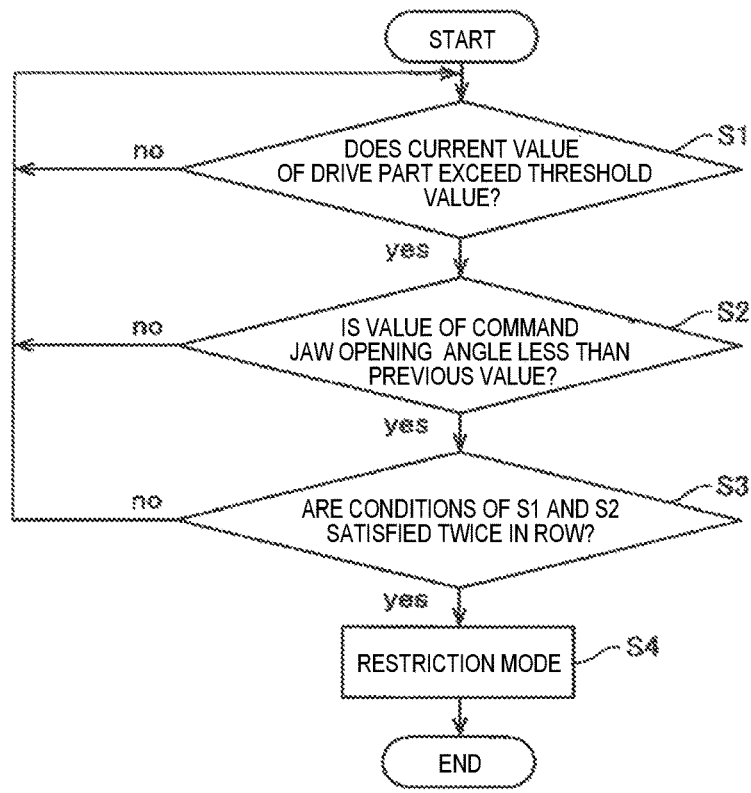
FIG. 16 is a diagram of a flowchart illustrating a control process of starting the restriction mode in a state where the input device is operated according to a first embodiment.

As illustrated in FIG. 16, first, in step S1, it is determined whether or not the motor current value of the drive part 212*a*, 212*b* exceeds the predetermined threshold value. That is, in step S1, it is determined whether or not the motor current value of the drive part 212*a*, 212*b* has increased due to the pair of jaw members 43*a* and 43*b* grasping the object T.

Specifically, in step S1, it is determined whether or not the motor current values of the drive part 212*a* exceeds the predetermined threshold value of the drive part 212*a* according to the above equation (1), or the motor current value of the drive part 212*b* exceeds the predetermined threshold value according to the above equation (1). If either the motor current value of the drive part 212*a* or the motor current value of the drive part 212*b* do not exceed the predetermined threshold value, the process of step S1 is repeated. If at least one of the motor current value of the drive part 212*a* and the motor current value of the drive part 212*b* exceeds the predetermined threshold value, the process proceeds to step S2.

Then, in step S2, it is determined whether or not the value of the command jaw opening angle generated corresponding to the opening angle between the pair of grip members 11*b* of the operation handle 11 is smaller than the previous value of the command jaw opening angle which is stored immediately before. If the value of the command jaw opening angle generated is not smaller than the previous value of the command jaw opening angle, the process proceeds to step S1. If the value of the command jaw opening angle generated is smaller than the previous value of the command jaw opening angle, the process proceeds to step S3. Note that, for example, upon proceeding from steps S1, S2, and S3 to step S1, the value of the command jaw opening angle is stored in the memory 25 as the previous value of the command jaw opening angle.

Then, in step S3, it is determined whether or not the conditions of steps S1 and S2 are satisfied twice in a row. If the conditions of steps S1 and S2 are not satisfied twice in a row, the process proceeds to step S1. If the conditions of steps S1 and S2 are satisfied twice in a row, the process proceeds to step S4.

Then, in step S4, the mode is switched to the restriction mode, and the value of the command jaw opening angle when the restriction mode is started is stored in the memory 25. In the restriction mode, the magnitude of the command jaw opening angle is restricted as described above. After that, the restriction mode is continued until the restriction mode is released (ended).

(Control Process of Releasing Restriction Mode)

Next, with reference to the flowchart of FIG. 17, a control process for releasing the restriction mode by the controller 24 in the following state is described below.

Figure 17:
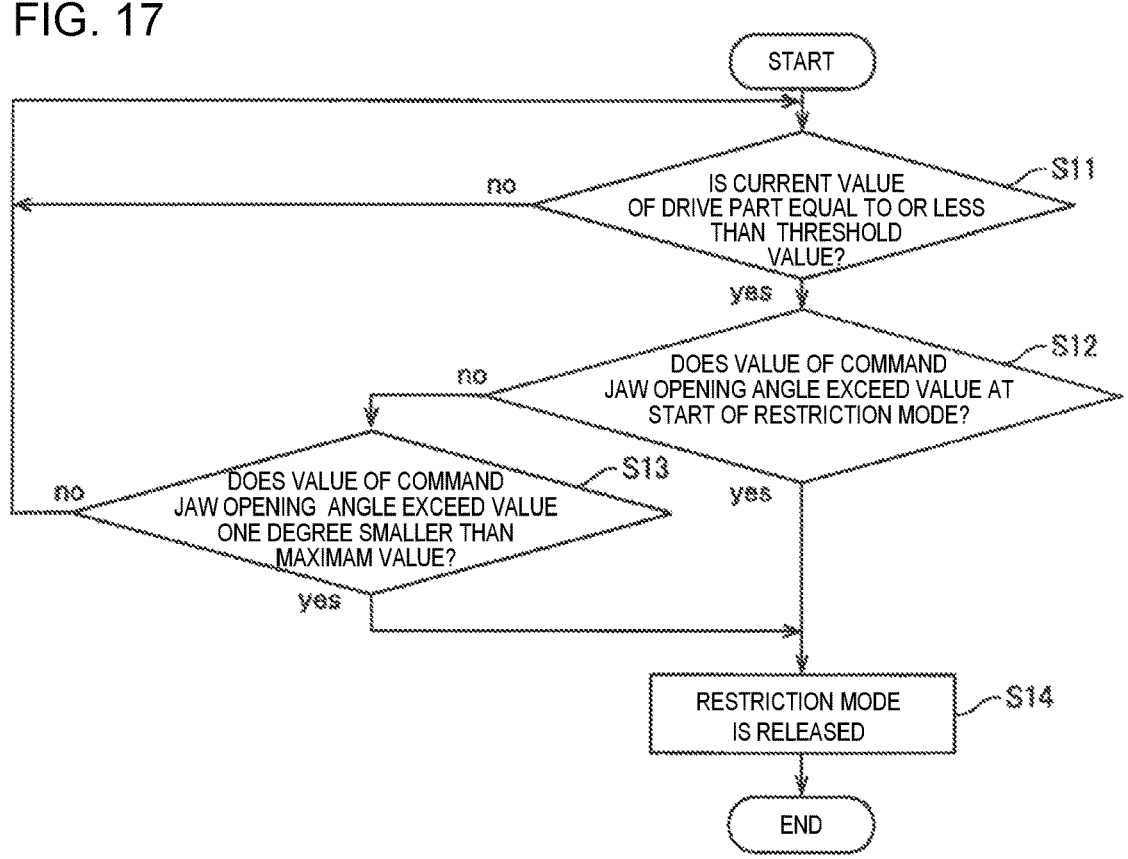
FIG. 17 is a diagram of a flowchart illustrating a control process of releasing (ending) the restriction mode in the state where the input device is operated according to a first embodiment.

As illustrated in FIG. 17, first, in step S11, it is determined whether or not the motor current values of the drive parts 212*a* and 212*b* are equal to or less than the predetermined threshold value. That is, in step S11, it is determined whether or not the motor current value of the drive part 212*a*, 212*b* has decreased because the pair of jaw members 43*a* and 43*b* no longer grasp the object T.

Specifically, in step S11, it is determined whether or not the motor current value of the drive part 212a gets equal to or less than the predetermined threshold value of the drive part 212a according to the above described equation (1), and the motor current value of the drive part 212b gets equal to or less than the predetermined threshold value for the drive part 212b according to the above described equation (1). If it is determined that both the motor current value of the drive part 212a and the motor current value of the drive part 212b are not equal to or less than the predetermined threshold value, the process of step S11 is repeated. If it is determined that both the motor current value of the drive part 212a and the motor current value of the drive part 212b are equal to or less than the predetermined threshold value, the process proceeds to step S12.

Then, in step S12, it is determined whether or not the value of the command jaw opening angle generated corresponding to the opening angle between the pair of grip members 11b of the operation handle 11 exceeds the value of the command jaw opening angle at the time of starting the restriction mode. If the value of the command jaw opening angle generated exceeds the value of the command jaw opening angle at the time of starting the restriction mode, the process proceeds to step S14. Then, in step S14, the restriction mode is released (ended).

Further, in step S12, if the value of the command jaw opening angle generated does not exceed the value of the command jaw opening angle at the time of starting the restriction mode, the process proceeds to step S13.

Then, in step S13, it is determined whether or not the value of the command jaw opening angle generated exceeds the value close to the maximum value of the command jaw opening angle (the approximate maximum value, e.g., a value one degree smaller than the maximum value). If the value of the command jaw opening angle generated does not exceed the value that is less than the approximate maximum value (e.g., the value one degree smaller than the maximum value), the process proceeds to step S11. If the value of the command jaw opening angle exceeds the approximate maximum value (e.g., the value one degree smaller than the maximum value), the process proceeds to step S14. Then, in step S14, the restriction mode is released (ended).

(Control Process of Releasing Restriction Mode)

Next, with reference to the flowchart of FIG. 18, the control process for releasing the restriction mode by the controller 24 in the out-of-following state is described below.

Figure 18:
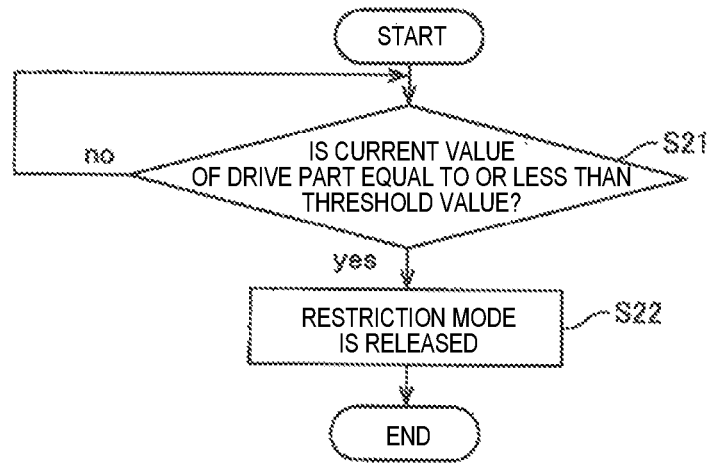
FIG. 18 is a diagram of a flowchart illustrating a control process of starting the restriction mode in a state where the input device is not operated according to a first embodiment.

As illustrated in FIG. 18, first, in step S21, it is determined whether or not the motor current value of the drive part 212a, 212b gets equal to or less than the predetermined threshold value. Note that the process of step S21 is the same as in step S11 illustrated in FIG. 17. That is, if it is determined that both the motor current value of the drive part 212a and the motor current value of the drive part 212b are not equal to or less than the predetermined threshold value, the process of step S21 is repeated. If it is determined that both the motor current value of the drive part 212a and the motor current value of the drive part 212b are equal to or less than the predetermined threshold value, the process proceeds to step S22. Then, in step S22, the restriction mode is released (ended). Unlike the control process for releasing the restriction mode during the following state illustrated in FIG. 17, in the control process for releasing the restriction mode during the out-of-following state illustrated in FIG. 18, the conditions (steps S12 and S13) of the command jaw opening angle do not determined.

Second Embodiment

Next, a second embodiment is described with reference to FIGS. 19 to 21. Unlike a first embodiment, in a restriction mode according to a second embodiment, the minimum value of the commanded jaw opening angle is limited to zero or less. The configurations in a second embodiment same as those of a first embodiment are designated by the same reference numerals in the drawings, and the description thereof may be omitted for avoid redundancy.

(Configuration of Robotic Surgical System)

Figure 19:
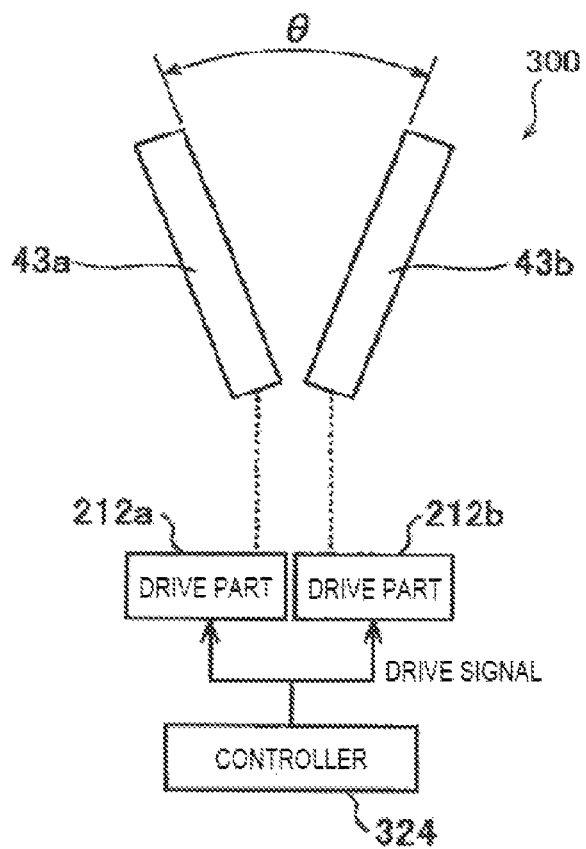
FIG. 19 is a diagram illustrating a pair of jaw members, drive parts, and a controller according to a second embodiment.

As illustrated in FIG. 19, a robotic surgical system 300 according to a second embodiment includes a controller 324 instead of the controller 24 of a first embodiment. Note that the controller 324 is an example of a controller or a control device.

Figure 20:
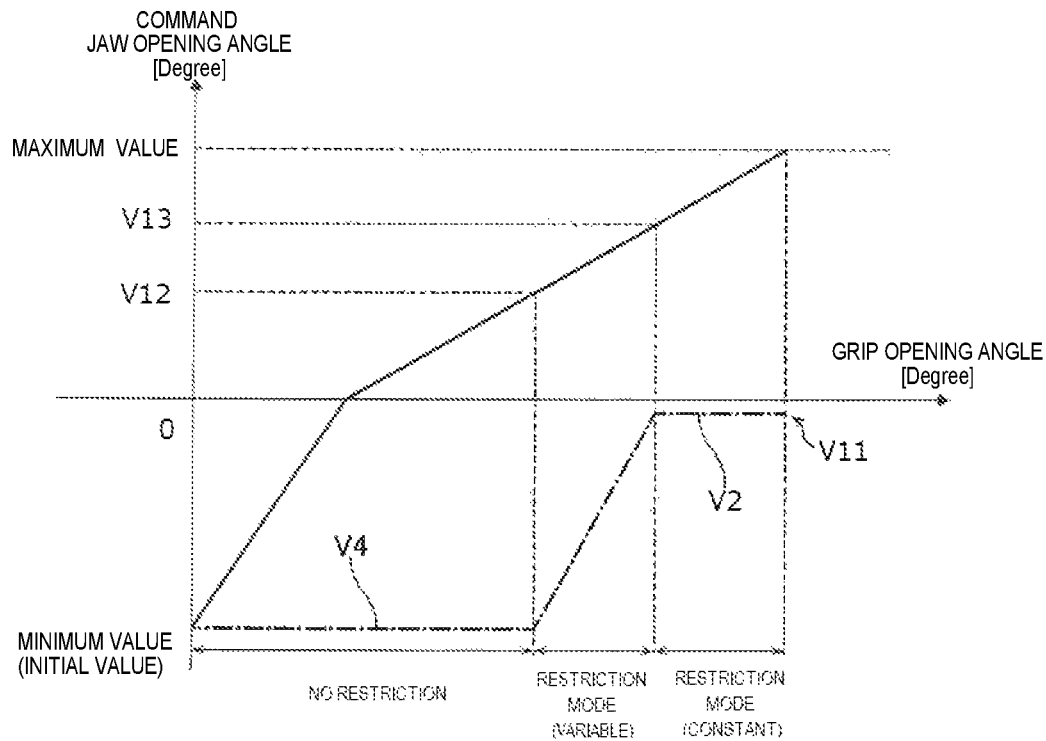
FIG. 20 is a graph for explaining a restriction mode according to a second embodiment.

FIG. 20 is a graph illustrating a relationship (indicated by a dash-dotted line) between a detected angle and the minimum value of the jaw command opening angle in addition to the relationship (the graph of FIG. 12) between the opening angle between the pair of grip members 11b of the operation handle 11 and the command jaw opening angle for the opening angle between the pair of jaw members 43a and 43b. In the graph illustrated in FIG. 20, the horizontal axis indicates the opening angle between the pair of grip members 11b, and the vertical axis indicates the command jaw opening angle for the opening angle between the pair of jaw members 43a and 43b. Note that the detected angle is the opening angle θ of the pair of jaw members 43a and 43b when the motor current value of the drive part 212a, 212b exceeds the predetermined threshold value. For example, the detected angle can be estimated from the rotation angle of the motor of the drive part 212a, 212b detected by the controller 324 when the motor current value of the drive part 212a, 212b exceeds the predetermined threshold value, with taking into account the elongation of the elongate element W.

Figure 21:
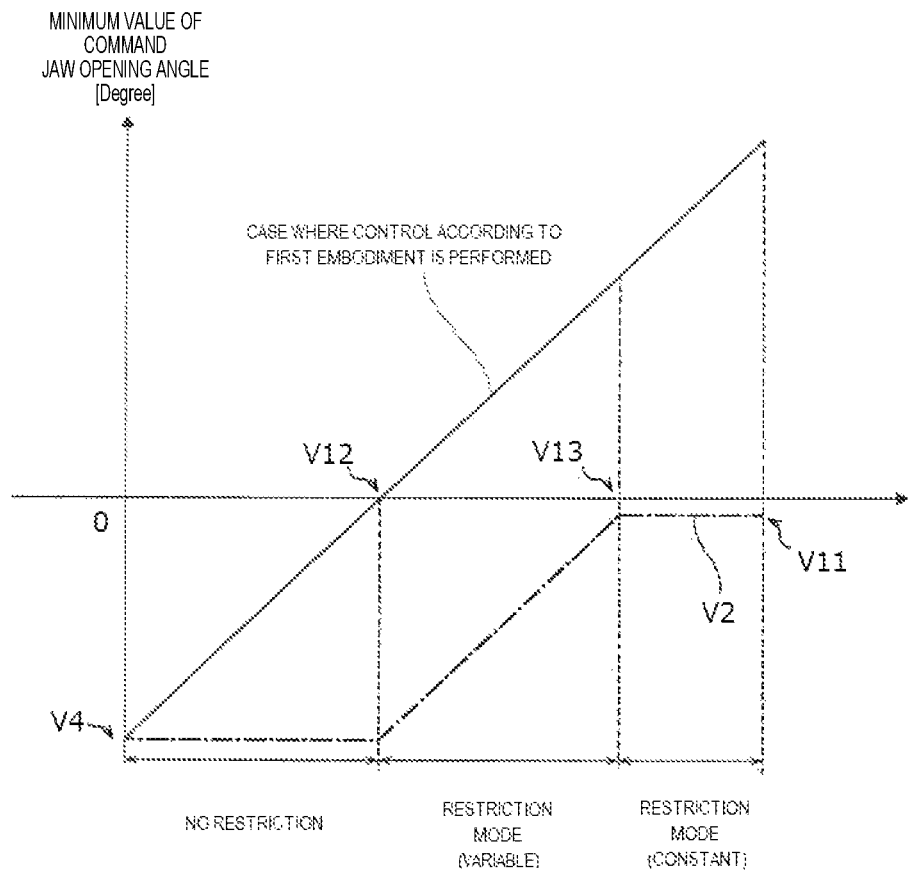
FIG. 21 is a graph illustrating a relationship between a detected angle and a minimum value of a command jaw opening angle according to a second embodiment.

FIG. 21 is a graph illustrating the relationship between the detected angle and the minimum value of the command jaw opening angle. In the graph illustrated in FIG. 21, the horizontal axis indicates the detected angle and the vertical axis indicates the minimum value of the command jaw opening angle for the opening angle between the pair of jaw members 43a and 43b. Further, in the graph of FIG. 21, the solid line indicates the relationship between the detected angle and the minimum value of the command jaw opening angle in the case where the control according to a first embodiment is performed, whereas the dot-dash line indicates the relationship between the detected angle and the minimum value of the commanded jaw opening angle in the case where the control according to a second embodiment is performed.

In a second embodiment, as illustrated in FIGS. 20 and 21, the controller 324 is configured, when it is determined that the motor current values of the drive parts 212a and 212b during the closing operation of the pair of jaw members 43a and 43b excesses the predetermined threshold value, drive the drive parts 212a and 212b in a restriction mode in which the minimum value V2 of the command jaw opening angle is set (restricted) to a value that is greater than the initial value V4 and is equal or less than zero. That is, in the restriction mode according to a second embodiment, not only the lower limit of the minimum value of the command jaw opening angle is restricted, but also the upper limit of the minimum value of the command jaw opening angle is restricted. Here, for example, in a case where the object T is a tissue and is pulled while being gripped by the pair of jaw members 43a and 43b, the thickness of the object T would become thinner. In a first embodiment described above, the minimum value of the command jaw opening angle for the pair of jaw members 43a and 43b may be greater than zero (see FIG. 21), and thus it may be possible that the object T may fall off the pair of jaw members 43a and 43b due to change in the thickness of the object T. To the contrary, in a second embodiment, even in the restriction mode, the minimum value of the commanded jaw opening angle is set to always be zero or less. Thus, even if the thickness of the object T changes, the pair of jaw members 43a and 43b is closed to follow the change in the thickness of the object T, so that the object T can be reliably grasped.

Further, in a second embodiment, the upper limit V11 of the minimum value V2 of the commanded jaw opening angle in the restriction mode is set. The upper limit value V11 is a negative value smaller than zero by a predetermined amount. Therefore, unlike a case where the upper limit value V11 is zero, even if a backlash between the jaw member 43a (43b) and the pulley 43d (43e) exits, the pair of jaw members 43a and 43b can be completely closed in the restricted mode. The upper limit value V11 is set to the negative value smaller by the predetermined amount corresponding to the backlash between the jaw member 43a (43b) and the pulley 43d (43e). For example, in a case where the backlash is 1.5 degrees, the upper limit value V11 is set to −1.5 degrees.

Further, in a second embodiment, the controller 324 is configured to, when it is determined that the motor current value of the drive part 212a or 212b exceeds the predetermined threshold value during the closing operation of the pair of jaw members 43a and 43b, detect the rotation angle of the motor at the time when the motor current value of the drive part 212a or 212b exceeds the predetermined threshold value, and to control, based on the detected rotation angle of the motor, whether or not to switch to the restriction mode (switching to the restriction mode). Specifically, the controller 24 is configured to, when it is determined that the motor current value of the drive part 212a or 212b exceeds the predetermined threshold value during the closing operation of the pair of jaw members 43a and 43b, determine whether or not the detected angle is equal to or greater than a predetermined value V12, and to switch to the restriction mode when the detected angle is equal to or greater than the predetermined value V12 and not to switch to the restriction mode when the detected angle is less than the predetermined value V12. As a result, it is possible to prevent unnecessary switching to the restriction mode in a range where the detected angle is small. When not switching to the restriction mode, the minimum value of the commanded jaw opening angle is the initial value V4.

Further, the controller 324 is configured to, when it is determined that the motor current value of the drive part 212a or 212b exceeds the predetermined threshold value during the closing operation of the pair of jaw members 43a and 43b and the detected angle exceeds the predetermined value V12, switch to the restriction mode. Specifically, the controller 324 is configured, when the detected angle is equal to or greater than the predetermined value V12 and less than a predetermined value V13 (V13>V12), to switch to the restriction mode in which the minimum value V2 of the command jaw opening angle is restricted to greater than the initial value V4 and less than the upper limit value V11. In this case, the controller 324 is configured to restrict the minimum value V2 of the commanded jaw opening angle so that the minimum value V2 of the commanded jaw opening angle gradually decreases as the detected angle decreases. For example, the controller 324 is configured to obtain the minimum value V2 of the commanded jaw opening angle according to Equation (2) below.

$$V2 = V4 \times R + V4 - c \quad (2)$$

V2: the minimum value of the command jaw opening angle in the restriction mode

V4: the initial value (the minimum value of the command jaw opening angle before the restriction mode)

R: a reduction ratio with respect to the detected angle (a variable that varies according to the detected angle)

c: a predetermined constant

Further, the controller 324 is configured, when the detected angle is equal to or greater than the predetermined value V13, to switch to the restriction mode in which the minimum value V2 of the commanded jaw opening angle is limited to the upper limit value V11. In this case, the controller 324 is configured to limit the minimum value V2 of the commanded jaw opening angle so that the minimum value V2 of the commanded jaw opening angle is set to the upper limit value V11 regardless of the value of the detected angle.

Modifications

Note that one or more embodiments disclosed herein should be considered as exemplary in all respects and do not limit the invention. The scope of the invention is indicated by claims, not by explanation of one or more embodiments described above, and includes equivalents to the claims and all alterations (modification) within the same.

In first and second embodiments described above, the case has been described in which the pair of jaw members are driven by the soft elongate elements formed of wires or cables. However, the invention is not limited thereto. For example, the pair of jaw members may be driven by rigid elongate elements such as rods or the like.

Further, in first and second embodiments described above, the case has been described in which the operation handle including the pair of grip members is provided as the input device for inputting the command to open and close the pair of jaw members. However, the invention is not limited thereto. For example, an operation handle other than the operation handle that includes the pair of grip members may be provided as an input device for inputting the command to open and close the pair of jaw members. Also, a device or the like other than the operation handle may be provided as an input device for inputting the command to open and close the pair of jaw members.

Further, in a first embodiment described above, the case has been described in which the predetermined value, which is, the difference between the value of the command jaw opening angle when the motor current value of the drive part exceeds the predetermined threshold value and the minimum value of the command jaw opening angle in the restriction mode is the same as the difference between the value of the command jaw opening angle when the opening angle between the pair of jaw members is zero and the initial minimum value of the command jaw opening angle. For example, the predetermined value may be a value larger than or smaller than the difference between the value of the jaw command opening angle when the opening angle between the pair of jaw members is zero and the initial minimum value of the jaw command opening angle.

Further, in first and second embodiments described above, the case has been described in which the controller is configured, when it is determined that the current value of the drive part excesses the predetermined threshold value and the value of the command jaw opening angle gets smaller than the previous value of the command jaw opening angle, to switch to the restriction mode. However, the invention is not limited thereto. For example, the controller may be configured, when it is detected that the motor current value of the drive part excesses the predetermined threshold value, to switch to the restriction mode regardless of the value of the command jaw opening angle.

Further, in first and second embodiments described above, the case has been described in which the controller is configured, when it is repeatedly determined multiple times that the current value of the drive part excesses the predetermined threshold value and the value of the command jaw opening angle gets smaller than the previous value of the command jaw opening angle, to switch to the restriction mode. However, the invention is not limited thereto. For example, the controller may be configured, when it is determined only once that the current value of the drive part excesses the predetermined threshold value and the value of the command jaw opening angle gets smaller than the previous value of the command jaw opening angle, to switch to the restriction mode.

Further, in first and second embodiments described above, the case has been described in which the controller is configured to release the restriction mode, when the motor current values of the drive parts get equal to or less than the predetermined threshold value and when the value of the command jaw opening angle generated exceeds the value of the command jaw opening angle at the start of the restriction mode or the value close to the maximum value of the command jaw opening angle (the approximate maximum value of the command jaw opening angle). However, the invention is not limited thereto. For example, the controller may be configured, when it is determined that the motor current values of the drive parts get equal to or less than the predetermined threshold value in the following state, to release the restriction mode regardless of the value of the command jaw opening angle.

In first and second embodiments described above, the case has been described in which the predetermined threshold value is set according to the above described equation (1). However, the invention is not limited thereto. For example, the predetermined threshold value may be set based on an equation other than the above described equation (1).

In first and second embodiments described above, the case has been described in which the fall-off prevention part is provided. However, the disclosure is not limited thereto. For example, the fall-off prevention part may not be provided.

In one or more embodiments described above, the case has been described in which the robotic surgical system is configured as a master-slave system. However, the disclosure is not limited thereto. For example, the robotic surgical system may be a system including a semi-automated process in which the patient-side apparatus automatically performs a part of the process without receiving instructions from the remote control apparatus, or including a fully automated process in which the patient-side apparatus performs the process independently. In such a case, the control unit or the controller generates the command jaw opening angle based on a control program including the restriction mode.

In a second embodiment described above, the case has been described in which the upper limit of the minimum value of the command jaw opening angle is set in the restriction mode. However, the invention is not limited thereto. For example, it is not necessary to set the upper limit of the minimum value of the jaw command opening angle in the restriction mode.

In a second embodiment described above, the case has been described in which the upper limit of the minimum value of the command jaw opening angle is a negative value smaller than zero by the predetermined amount. However, the invention is not limited to this. For example, the upper limit may be zero.

The functions of each of the elements disclosed herein may be carried out by a circuitry or a processing circuitry including a general purpose processor, a dedicated processor, an integrated circuit, an ASIC (Application Special Integrated Circuit), a conventional circuit, or a combination of two or more of them, that is configured or programmed to perform the functions. A processor is considered a processing circuitry or a circuitry because it contains transistors and other circuit elements. In the disclosure, a circuit, a unit, or a means may be either a hardware that is configured to perform the recited function(s) or a hardware that is programmed to perform the recited function(s). The hardware may be the hardware disclosed herein, or may be other known hardware that is programmed or configured to perform the function(s) described. If the hardware is a processor which is considered as a type of a circuit, a circuit, a means, or a unit is a combination of hardware and software, and the software is used to configure the hardware and/or the processor.

The invention claimed is:

1. A robotic surgical system comprising:
a surgical instrument including a pair of jaw members configured to be driven by elongate elements connected to a driven member so as to be opened and closed to grasp an object;
an input device to which a command for opening and closing the pair of jaw members is to be input; and
a surgical robot that includes a robot arm to which the surgical instrument is attached and which includes a drive part configured to drive the driven member, and a controller configured to drive the drive part based on a command jaw opening angle associated with an input to the input device for controlling an opening angle between the pair of jaw members, wherein
the controller is configured to determine whether or not a current value of the drive part excesses a predetermined threshold value during a closing operation of the pair of jaw members and, when it is determined that the current value of the drive part excesses the predetermined threshold value, to drive the drive part in a restriction mode in which a magnitude of the command jaw opening angle is restricted.

2. The robotic surgical system according to claim 1, wherein
the controller is configured, when it is determined that the current value of the drive part excesses the predetermined threshold value during the closing operation of the pair of jaw members, to drive the drive part in the restriction mode in which a minimum value of the command jaw opening angle is restricted to a value greater than an initial minimum value of the command jaw opening angle, which is the minimum value of the command jaw opening angle in a mode other than the restriction mode.

3. The robotic surgical system according to claim 2, wherein
a difference between the value of the command jaw opening angle when the current value of the drive part exceeds the predetermined threshold value and the minimum value of the command jaw opening angle in the restriction mode is set same as a difference between the value of the command jaw opening angle that makes the opening angle between the pair of jaw members zero degrees and the initial minimum value.

4. The robotic surgical system according to claim 1, further comprising
a storage configured to store the value of the command jaw opening angle at predetermined intervals, wherein
the controller is configured, when it is determined that the current value of the drive part excesses the predetermined threshold value and the value of the command jaw opening angle gets smaller than the value of the command jaw opening angle that is stored in the storage, to switch to the restriction mode.

5. The robotic surgical system according to claim 4, wherein
the controller is configured, when it is repeatedly determined multiple times that the current value of the drive part excesses the predetermined threshold value and the value of the command jaw opening angle gets smaller than the value of the command jaw opening angle that is stored in the storage, to switch to the restriction mode.

6. The robotic surgical system according to claim 1, wherein
the controller is configured, when the current value of the drive part gets equal to or smaller than the predetermined threshold value, to release the restriction mode.

7. The robotic surgical system according to claim 6, wherein
in a state where the surgical instrument is operable by the input device, the controller is configured to release the restriction mode, when the current value of the drive part gets equal to or less than the predetermined threshold value and the value of the command jaw opening angle exceeds the value of the command jaw opening angle at a start of the restriction mode or a value close to a maximum value of the command jaw opening angle.

8. The robotic surgical system according to claim 7, wherein
the surgical robot includes a second robot arm to which an endoscope is to be attached,
the robotic surgical system further comprises a display configured to display an image captured by the endoscope,
the display incudes a sensor configured to detect a presence of an operator,
the controller is configured, when the sensor of the display detects the presence of the operator, to determine that the surgical instrument is operable by the input device.

9. The robotic surgical system according to claim 6, wherein
in a state where the surgical instrument is not operable by the input device, the controller is configured, when the current value of the drive part gets equal to or smaller than the predetermined threshold value, to release the restriction mode regardless of the value of the command jaw opening angle.

10. The robotic surgical system according to claim 9, wherein
the surgical robot includes a second robot arm to which an endoscope is to be attached,
the robotic surgical system further comprises a display configured to display an image captured by the endoscope,
the display incudes a sensor configured to detect a presence of an operator,
the controller is configured, when the sensor of the display does not detect the presence of the operator, to determine that the surgical instrument is not operatable by the input device.

11. The robotic surgical system according to claim 1, wherein
the predetermined threshold value is set based on a frictional force of the drive part.

12. The robotic surgical system according to claim 1, wherein
the elongate elements are composed of wires or cables,
the surgical instrument further includes pulleys around which the elongate elements to drive the pair of jaw members are wound,
the pulleys include engagement portions engaged with the pair of jaw members for driving the jaw members, and
the pair of jaw members is configured, when the pulleys are rotated about a rotational axis of the pulleys, to be opened and closed about a rotational axis different from the rotational axis of the pulleys.

13. The robotic surgical system according to claim 2, wherein
the controller is configured, when it is determined that the current value of the drive part excesses the predetermined threshold value during the closing operation of the pair of jaw members, to drive the drive part in the restriction mode in which the minimum value of the command jaw opening angle is restricted to the value greater than the initial minimum value of the command jaw opening angle and not greater than zero.

14. The robotic surgical system according to claim 13, wherein
an upper limit of the minimum value of the commanded jaw opening angle in the restriction mode is set to a negative value less than zero by a predetermined amount.

15. The surgical robot according to claim 13, wherein
the controller is configured to detect the opening angle between the pair of jaw members at a time when the current value of the drive part excesses the predetermined threshold value, and configured not to switch to the restriction mode, when the detected opening angle between the pair of jaw members is less than a predetermined value even when it is determined that the current value of the drive part excesses the predetermined threshold value during the closing operation of the pair of jaw members.

16. A robotic surgical method for a robotic surgical system, the robotic surgical system comprising: a surgical instrument including a pair of jaw members configured to be driven by elongate elements connected to a driven member so as to be opened and closed to grasp an object; an input device to which a command for opening and closing the pair of jaw members is to be input; and a surgical robot including a robot arm to which the surgical instrument is attached and which includes a drive part configured to drive the driven member, the robotic surgical method comprising:
obtaining a command jaw opening angle that is associated with an input to the input device for controlling an opening angle between the pair of jaw members; and driving the drive part based on the command jaw opening angle, wherein driving the drive part comprises: determining whether or not a current value of the drive part excesses a predetermined threshold value during a closing operation of the pair of jaw members; and when it is determined that the current value of the drive part excesses the predetermined threshold value, driving the drive part in a restriction mode in which a magnitude of the command jaw opening angle is restricted.

17. A surgical robot comprising:

a surgical instrument including a pair of jaw members configured to be driven by elongate elements connected to a driven member so as to be opened and closed to grasp an object;

a robot arm to which the surgical instrument is attached and including a drive part configured to drive the driven member;

a controller configured to drive the drive part based on a command jaw opening angle for an opening angle between the pair of jaw members, wherein the controller is configured to determine whether or not a current value of the drive part exceeds a predetermined threshold value during a closing operation of the pair of jaw members, and when it is determined that the current value of the drive part exceeds the predetermined threshold value, to drive the drive part in a restriction mode in which a magnitude of the command jaw opening angle is restricted.

18. The surgical robot according to claim 17, wherein the controller is configured, when it is determined that the current value of the drive part excesses the predetermined threshold value, to drive the drive part in the restriction mode in which a minimum value of the command jaw opening angle is restricted to a value greater than an initial minimum value of the command jaw opening angle, which is the minimum value of the command jaw opening angle in a mode other than the restriction mode.

19. The surgical robot according to claim 18, wherein a difference between the value of the command jaw opening angle when the current value of the drive part exceeds the predetermined threshold value and the minimum value of the command jaw opening angle in the restriction mode is set same as a difference between the value of the command jaw opening angle that makes the opening angle between the pair of jaw members zero degrees and the initial minimum value.

20. The surgical robot according to claim 17, further comprising a storage configured to store the value of the command jaw opening angle at predetermined intervals, wherein the controller is configured, when it is determined that the current value of the drive part excesses the predetermined threshold value and the value of the command jaw opening angle gets smaller than the value of the command jaw opening angle that is stored in the storage, to switch to the restriction mode.

* * * * *